United States Patent
Kowalewski et al.

(10) Patent No.: US 7,464,583 B1
(45) Date of Patent: Dec. 16, 2008

(54) METHODS AND APPARATUSES USING PROXIMAL PROBES

(75) Inventors: Tomasz P. Kowalewski, Pittsburgh, PA (US); Justin Allen Legleiter, San Francisco, CA (US)

(73) Assignee: Carnegie Mellon University, Pittsburgh, PA (US)

( * ) Notice: Subject to any disclaimer, the term of this patent is extended or adjusted under 35 U.S.C. 154(b) by 111 days.

(21) Appl. No.: 11/450,074

(22) Filed: Jun. 9, 2006

Related U.S. Application Data

(60) Provisional application No. 60/689,668, filed on Jun. 10, 2005.

(51) Int. Cl.
*G01N 11/10* (2006.01)
(52) U.S. Cl. ........................................................ 73/105
(58) Field of Classification Search ................ 73/105
See application file for complete search history.

(56) References Cited

U.S. PATENT DOCUMENTS

| | | | | |
|---|---|---|---|---|
| 5,995,704 | A * | 11/1999 | Shido | 386/46 |
| 6,311,549 | B1 * | 11/2001 | Thundat et al. | 73/54.24 |
| 6,335,522 | B1 * | 1/2002 | Shimada et al. | 250/201.3 |
| 6,763,322 | B2 * | 7/2004 | Potyrailo et al. | 702/189 |
| 6,891,626 | B2 * | 5/2005 | Niu et al. | 356/625 |
| 6,928,628 | B2 * | 8/2005 | Seligson et al. | 716/4 |
| 7,111,256 | B2 * | 9/2006 | Seligson et al. | 716/4 |
| 7,126,700 | B2 * | 10/2006 | Bao et al. | 356/625 |
| 2002/0189330 | A1 * | 12/2002 | Mancevski et al. | 73/105 |
| 2003/0130823 | A1 * | 7/2003 | Potyrailo et al. | 702/189 |

OTHER PUBLICATIONS

Sahin O., Magonov S., Su C., Quate C.F., Solgaard, O., An atomic force microscope tip designed to measure time-varying nanomechanical forces, Nature Nanotechnology 2, Jul. 29, 2007, pp. 507-514. (Abstract only).

Chen G.Y., Warmack R. J., Oden, P.I., Thundat, T., Transient response of tapping scanning force microscopy in liquids, J. Vac Sci. Technol. Mar./Apr. 1996, pp. 1313-1317, B 14(2), American Vacuum Society.

Cleveland J.P., Anczykowski, B., Schmid, A.E., Elings, V.B., Energy dissipation in tapping-mode atomic force microscopy, Appl. Phys. Lett., May 18, 1998, pp. 2613-2615, vol. 72, No. 20, American Institute of Physics.

Putman, C.A.J., Van Der Werf, K.O., De Grooth, B.G., Van Hulst, N.F., Greve, J., Tapping mode atomic force microscopy in liquid Appl. Phys. Lett., May 2, 1994, pp. 2454-2456, 64(18), American Institute of Physics.

(Continued)

*Primary Examiner*—Michael Cygan
(74) *Attorney, Agent, or Firm*—Thorp Reed & Armstrong, LLP

(57) ABSTRACT

Apparatuses and methods for using proximal probes. A method includes measuring motion of an oscillating probe, producing a signal indicative of motion of the oscillating probe, and filtering the signal indicative of motion of the oscillating probe. In one embodiment, filtering includes performing signal decomposition to produce a filtered signal. In another form, filtering includes performing a Fourier transform, comb filtering in the frequency domain, and performing an inverse Fourier transform to produce a filtered signal. In another embodiment, filtering includes amplifying specific frequencies of the signal indicative of motion of the oscillating probe. Apparatuses according to the present invention are also provided.

24 Claims, 17 Drawing Sheets

OTHER PUBLICATIONS

Putman, C.A.J., Van Der Werf, K.O., De Grooth, B.G., Van Hulst, N.F., Greve, J. Visoelasticity of Living Cells Allows High Resolution Imaging by Tapping Mode Atomic Force Microscopy, Biophysical Journal, Oct. 1994, pp. 1749-1753, vol. 67, Biophysical Society.

Hillenbrand, R., Stark, M., Guckenberger, R., Higher-harmonics generation in tapping-mode atomic-force microscopy: Insights into the tip-sample interaction, Appl. Phys. Lett., Jun. 5, 2000, pp. 3478-3480, vol. 76, No. 23 American Institute of Physics.

Legleiter, J., Kowalewski, T., Insights into fluid tapping-mode atomic force microscopy provided by numerical simulations, Appl. Phys. Lett., Oct. 14, 2005, pp. 163120-1 to 163120-3, 87, American Institute of Physics.

Sahin, O., Yaralioglu, G., Grow, R., Zappe, S.F., Atalar, A., Quate, C., Solgaard, O., High-Resolution imaging of elastic properties using harmonic cantilevers, Sensors and Actuators A, 2004, pp. 183-190, 114, Science Direct.

Stark, M., Stark, R.W., Heckl, W.M., Guckenberger, R., Inverting dynamic force microscopy: From signals to time-resolved interaction forces, PNAS, Jun. 25, 2002, pp. 8473-8478, vol. 99, No. 13.

Stark, R.W., Heckl, W.M., Higher harmonics imaging in tapping-mode atomic-force microscopy Rev. Sci. Instrum., Dec. 2003, pp. 5111-5114, vol. 74, No. 12, American Institute of Physics.

Tamayo, J., Garcia, R. Relationship between phase shift and energy dissipation in tapping-mode scanning force microscopy, Appl. Phys. Lett. Nov. 16, 1998, pp. 2926-2928, vol. 73, No. 20, American Institute of Physics.

Tamayo, J., Energy dissipation in tapping-mode scanning force microscopy with low quality factors, Appl. Phys. Lett. Nov. 29, 1999, pp. 3569-3571, vol. 75, No. 22, American Institute of Physics.

Todd, B.A., Eppell, S.J., Inverse problem of scanning force microscope force measurements, J. Appl. Phys, Sep. 1, 2003, pp. 3563-3572, vol. 94, No. 5, American Instsitute of Physics.

* cited by examiner

METHODS AND APPARATUSES USING PROXIMAL PROBES

CROSS-REFERENCE TO RELATED APPLICATIONS

This application claims priority from U.S. Provisional Patent Application No. 60/689,668, filed Jun. 10, 2005, which is incorporated herein by reference.

STATEMENT REGARDING FEDERALLY-SPONSORED RESEARCH AND DEVELOPMENT

This invention was made, in part, with government support under Grant Numbers NW STS-0304568 awarded by the National Science Foundation and DMR-9974457 awarded by the National Science Foundation. The United States government may have certain rights in this invention.

FIELD OF THE INVENTION

The present invention is directed generally to methods and apparatuses using proximal probes and related apparatuses and methods.

BACKGROUND OF THE INVENTION

Tapping mode atomic force microscopy (TMAFM) is a widely used dynamic imaging technique that maps surface topography by monitoring the oscillation amplitude of a cantilever integrated with an ultra-sharp tip probe, driven by a piezoelectric bimorph element mounted at the cantilever root, as described in several issued US patents. In this imaging mode, the cantilever is commonly driven near its resonance frequency $\omega_o$, and the intermittent tip-sample contacts lead to the decrease of cantilever oscillation amplitude from the "free" amplitude $A_o$ to tapping amplitude A. The sample surface acts as a repulsive barrier that limits the tapping amplitude of the cantilever. For a rigid surface, this decrease of cantilever oscillation amplitude is linear with the decrease of the distance between the tip and the sample $D_o$. Thus, the surface topography can be tracked by rastering the tip in the xy plane and using a feedback loop to continuously adjust the vertical (z) extension of the piezoelectric scanner to maintain the constant set-point $s=A/A_o$. The technique of scanning probe acceleration microscopy (SPAM) builds upon current proximal probe technology and instrumentation. Such techniques include jumping mode AFM, tapping mode AFM, fluid tapping mode AFM with a replaceable fluid cell excited acoustically and magnetically, and other variations of scanning probe microscopy with cantilever driven near its natural frequency.

There is considerable interest in using tapping mode AFM to study elastic and viscoelastic mechanical properties of surfaces, which would be beneficial in enhancing the ability to characterize materials and map mechanical and/or chemical variations of surfaces at the nanoscale in a much gentler fashion. Such information would be particularly useful in elucidating changes in biologically relevant surfaces such as lipid bilayers, cell surfaces, and other biomacromolecular complexes exposed to various factors. This could be particularly useful in elucidating potential effects of beta amyloid (a peptide implicated in Alzheimer's disease) or other peptides (such as those associated with conformational disease) on such surfaces that may modulate their mechanical properties.

Much of this information can be ascertained from the time-resolved force interaction between the surface and tip, but currently there is not a straightforward manner to obtain these force trajectories in tapping mode. In the absence of such a straightforward technique, the phase of the cantilever in tapping mode is commonly used to glean some information about the mechanical properties of surfaces; however, multiple sources of energy dissipation (i.e. capillary forces, viscoelasticity of the sample, cross talk with topography, etc.) make it difficult to interpret phase images. There is also a significant contribution due to frictional forces associated with the tilt of the cantilever and/or surface.

A more complete insight into the mechanical properties of the sample can be obtained by deeper analysis of the cantilever deflection trajectory involving studying its higher harmonic content. When the harmonic drive signal is applied to the cantilever, the resulting oscillation is also harmonic. When the tip taps the surface, the harmonic motion of the cantilever is distorted at the bottom of each oscillation cycle, resulting in anharmonicity, which shifts a certain amount of power to higher harmonics. In traditional TMAFM, which monitors cantilever deflection only at the oscillation frequency, information about anharmonicity is lost. The easiest way to retain it is by digitizing the entire cantilever trajectory at sufficiently high frequency (at least twice the frequency of the highest harmonic) and high bit resolution. Recent developments in the area of high-speed A/D converters make this task entirely possible. When using higher harmonics to reconstruct the tip-sample force interaction per oscillation cycle, the transfer function of the cantilever detection system must also be known, and this can be difficult to obtain. Currently, the most straightforward method of measuring the transfer function of a cantilever involves studying the oscillation decay of a cantilever subjected to an initial deflection. The initial deflection can be provided by running a force curve experiment on a strongly adhesive surface. It must also be noted that there are other sources of anharmonicity in cantilever deflection signals. These include nonlinearities of the detector and electronics of the AFM. Also, higher eigenmodes of the cantilever can complicate analysis based on higher harmonics. Based on this, efforts have been made to produce cantilevers with well defined eigenmodes to enhance the higher harmonic content in tapping mode AFM signals. Another common problem in analyzing higher harmonics is the rapid decay of the harmonic envelope, which can effectively place them below the noise level.

Accordingly, there is a need for improved scanning probe acceleration microscopy. Those and other advantages of the present invention will be described in more detail hereinbelow.

BRIEF SUMMARY OF THE INVENTION

In one embodiment, the present invention is an apparatus including a proximal probe including an oscillating probe and including an output port for carrying a cantilever deflection signal, and a signal filter connected to the output port of the proximal probe. The filter can take several forms. In one form, the filter includes a signal processor including computer readable instructions which, when executed, cause a signal at the input to be decomposed and producing a filtered signal. In another form, the filter includes a signal processor including computer readable instructions which, when executed, cause a signal at the input to be subject to a Fourier transform, comb filtered in the frequency domain, and subject to an inverse Fourier transform to produce a filtered signal. In other forms, the filter may be implements as a plurality of frequency-specific amplifiers each having an input connected to the input of the filter, and wherein the outputs of the frequency-specific amplifiers are connected together to collectively produce a filtered signal.

In another embodiment, the present invention includes a method for performing proximal probing, including measuring deflection of an oscillating probe, producing a signal indicative of deflection of the oscillating probe, and filtering the signal indicative of deflection of the oscillating probe. Filtering can be performed in several ways. In one embodiment, filtering includes performing signal decomposition to produce a filtered signal. In another form, filtering includes performing a Fourier transform, comb filtering in the frequency domain, and performing an inverse Fourier transform to produce a filtered signal. In another embodiment, filtering includes amplifying specific frequencies of the signal indicative of deflection of the oscillating probe.

In some embodiments, the present invention includes a method that allows for the recovery of the time-resolved interaction force between a proximal probe tip and a surface of interest. This method is based on taking the second derivative (or acceleration) of the cantilever deflection signal, which when properly scaled corresponds directly to the tip/sample force. To overcome the noise inherent to the cantilever deflection signal, a comb filter based on the Fourier transform may be used.

According to another embodiment of the present invention, single level or multiple level signal decomposition may be used to filter the signals in the time domain. Single level or multiple level signal decomposition may be implements, for example, with single level or multiple level wavelet processing or analysis.

According to another embodiment of the present invention, the comb filter and wavelets can be used in combination. Filtering with Fourier transforms and comb filters, or with signal decomposition, or with combinations thereof, may be implemented with one or more signal processors which perform the desired processes on analog or digital signals.

Alternatively, a more hardware-oriented approach may be used in which a plurality of frequency-specific amplifiers are used. The reconstructed time-resolved force trajectories contain information about local surface properties, such as modulus, adhesion, and specific binding. This method and apparatuses according to the present invention allows for studying these properties with nanoscale spatial resolution.

Many variations are possible with the present invention. These and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein.

DETAILED DESCRIPTION OF THE INVENTION

Figure 1:
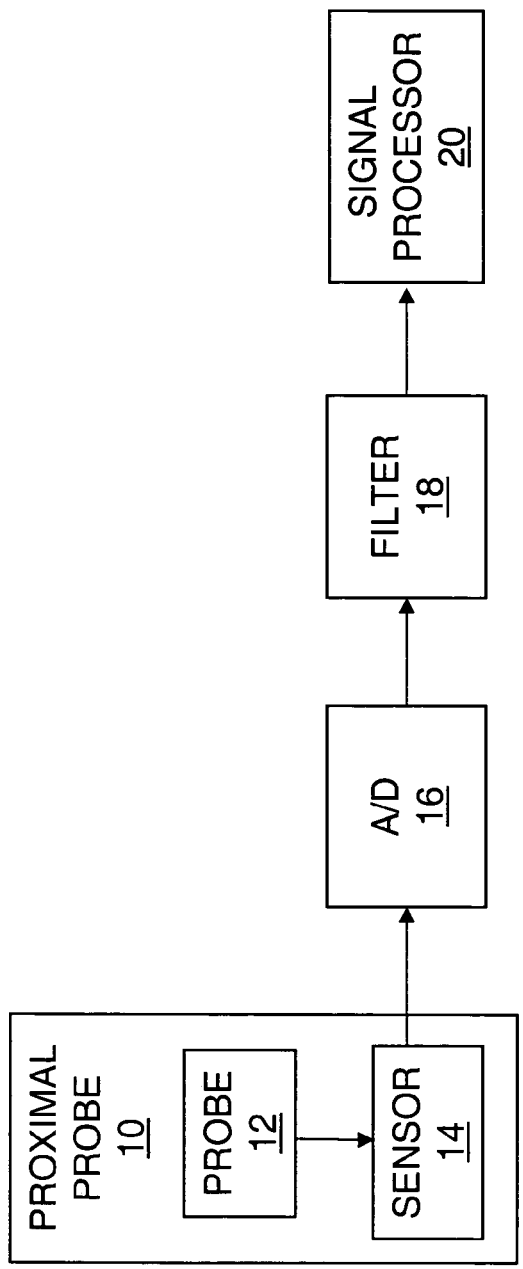
FIG. 1 illustrates one embodiment of an apparatus according to the present invention.

FIG. 1 illustrates one embodiment of an apparatus according to the present invention. In that embodiment, a proximal probe 10 includes an oscillating probe 12 and sensor 14. The proximal probe 10 produces a signal indicative of motion of the probe 12. The signal indicative of motion of the probe 12 is provided to an analog-to-digital (A/D) converter 14, which converts the motion signal from an analog signal to a digital signal. A filter 18 receives the digital signal and filters it. The filtered signal is provided to a signal processor 20 for further processing.

The proximal probe 10 may be, for example, an atomic force microscope (AFM). The present invention will generally be described in terms of an AFM, although other forms of a proximal probe 10 may also be used with the present invention. In addition, the present invention will generally be described in terms of tapping mode operation, although the present invention is also applicable to non-contact operation. In non-contact operation, the oscillation of the probe 12 will still be distorted, such as by magnetic, electrostatic, and other forces. Regardless of the mode of operation, the teachings of the present invention are applicable. Furthermore, the present invention will generally be described in terms of samples having time independent properties. However, the present invention is also applicable to situations where the sample or surface has time dependent properties. For example, some materials have a time dependent Young's modulus (i.e. are viscoelastic) and other time-dependent properties. The methods and apparatuses of the present invention can be used to resolve tip interaction with samples or surfaces having time-dependent properties.

In tapping mode, the probe 12 oscillates and contacts a sample or surface to be measured. In non-contact mode, the probe 12 oscillates and is deflected when it comes into close proximity to the sample or surface. The motion of the probe 12 is measured by the sensor 14. Measuring the motion of the probe 12 may include measuring deflection of the probe 12 by the surface, it may be measuring other interference with motion of the probe 12, it may be measuring the shape or change in shape of the probe, it may include measuring the position of the probe 12, or it may include other measurements related to or indicative of motion of the probe 12. Motion of the probe 12 may be measured at any part of the probe 12, including the free end, the base, or any other part or associated part of the probe 12 that is indicative or position, location, deflection, shape, distortion, or the like. The sensor 14 produces a signal indicative of motion which is output from the AFM 10. The probe 12 typically takes the form of a cantilevered structure, although the present invention is not limited to AFMs 10 with cantilevered probes 12. The characteristic of motion often measured is deflection, and the present invention will generally be described in terms of measuring deflection, although the present invention is also applicable to other measurements of motion other than, or in addition to, deflection.

The analog-to-digital converter 16 may be provided to convert analog signals from the AFM 10 to digital signals for further processing. The A/D converter 16 may be located in the AFM 10, in the filter 18, or external to both the AFM 10 and the filter 18. Alternatively, the sensor 14 may produce digital signals and the A/D converter 16 may be omitted. In another embodiment, analog signal processing may be used and the A/D converter 16 is not needed. In other embodiments, the sensor 14 may produce digital signals or other signal formats that do not need to be converted. Other variations and modifications are also possible.

The filter 18 is used to filter the deflection signal from the AFM 10. The filter 18 may take on many forms. For example, the filter 18 may filter signals in the time domain or in the frequency domain. In one embodiment, the filter 18 performs signal decomposition of the deflection signal. The signal decomposition may be single level signal decomposition or multiple level signal decomposition. For example, the signal decomposition may be in the form of wavelet analysis, which may be single level wavelet analysis or multiple level wavelet analysis. The particular wavelet type to be used in the wavelet analysis will vary depending on the application and the particular results desired from the analysis.

In another embodiment, the filter 18 may perform a Fourier transform of the deflection signal, followed by a filtering of the Fourier transformed signal in the frequency domain, followed by an inverse Fourier transform to return the filtered signal to the time domain. As will be described in more detail hereinbelow, it has been found that good results are achieved with a comb filter of the Fourier transform when the comb filter passes signals at integer harmonics of the resonant frequency of the cantilever or probe 12. The portions of the signal that are not at integer harmonics of the resonant frequency of the cantilever or probe 12 are attenuated. In general, the more harmonics captured or passed by the comb filter the better the results, although it is not necessarily required to capture every harmonic above the noise level.

In some embodiments one or more harmonic are intentionally attenuated to achieve particular results. In other embodiments of the present invention, frequencies other than integer harmonics may be captured or amplified or otherwise used. For example, sub-harmonics, sidebands, or other parts of the signal spectrum may be used according to the present invention. In some embodiments, a combination of harmonic and non-harmonic frequencies may be used. In some embodiments, the signal is filtered with regularly-spaced frequency pass bands that may or may not correspond to the harmonics of the cantilever or probe 12. Similarly, the signal may be filtered with regularly-spaced phase pass bands which may or may not correspond with the harmonics of the cantilever or probe 12.

In another embodiment, the filter 18 may filter the deflection signal by frequency, phase, or both. For example, the filter 18 may perform frequency-specific amplification of the signal. Alternatively, the filter may perform phase-specific amplification. In other embodiments, the filter 18 may perform frequency-specific or phase-specific attenuation of the deflection signal. For example, lock-in amplifiers may be used to selectively amplify certain frequencies of the deflection signal, while not amplifying, or attenuation, other frequencies. In other embodiments, filters, such as band pass filters, may be used to selectively filter or attenuate the deflection signal, after which selective portions of the filtered deflection signal may be amplified. Other variations and modifications are also possible.

The filter 18 may be implemented, for example, as one or more signal processors. The signal processors may be controlled by software to perform the desired signal processing. For example, the signal processors may include computer readable instructions which, when executed, cause the signals to be processed in a particular manner. In other embodiments, the signal processor 20 may be implemented in hardware or in a combination of hardware and software.

In one embodiment, one signal processor may perform a Fourier transform of the deflection signal, a second signal processor may perform the comb filtering, and a third signal may perform the inverse Fourier transform on the comb-filtered signal. In another embodiment, a single signal processor may perform all processes. In another embodiment, the filter 18 may be more hardware oriented. For example, a plurality of frequency-specific amplifiers may be used to selectively amplify signals at particular frequencies. For example, one or more frequency-specific amplifier may be provided for each harmonic of the resonant frequency of the cantilever or probe 12. As a result, the frequency-specific amplifiers will collectively filter the deflection signal without the need to perform a Fourier transform.

The signal processor 20 may be included to provide for further signal processing. As described hereinabove, the signal processor 20 may include computer readable instructions which, when executed, cause the signals to be processed in a particular manner. In other embodiments, the signal processor 20 may be implemented in hardware or in a combination of hardware and software. As will be described in more detail hereinbelow, it has been found that the second derivative of the filtered signal produces useful information for atomic force microscopy. Accordingly, the signal processor 20 may calculate the second derivative the filtered signal from the filter 18, and output a signal indicative of the second derivative. The signal processor 20 may also perform calculations and signal processing in addition to or in place of calculating the second derivative. For example, the signal processor 20 may perform additional calculations and signal processing using the second derivative of the filtered signal determine the tip/sample force between the probe 12 and the sample material. The signal processor 20 may perform other calculations and signal processing, such as using the second derivative to calculate the local sample modulus, to calculate the local sample adhesion, to calculate the local sample viscoelastic properties, and to calculate other properties. The signal processor 20 may also perform signal processing and calculation based on values other than the second derivative of the filtered signal. For example, the signal processor 20 may calculate the first derivative, the third derivative, or other signal processing of the signal from the filter 18. In some embodiments, the third derivative may be used, for example, to determine how sharply a force changes. Soft materials will result in a "blunted" force, and hard materials will result in a "sharp" force. Other derivatives and other forms of the signal may also be used according to the present invention. Values other than derivatives may also be used with the present invention.

The signal processor 20 may be implemented as one or more individual software-driven signal processors working together or independently. In other embodiments, the signal processor 20 may be implemented in hardware to perform the desired signal processing functions, or with a combination of hardware and software. In some embodiments, the signal processor 20 is separate from the filters 18. In other embodiments, the signal processor 20 is integrated with the filter 18.

Many variations are possible with the apparatus according to the present invention. For example, the probe 12 may be operated in a liquid, a gas environment, or a vacuum. In addition, the probe 12 may include a functionalized attachment. In one embodiment, the functionalized attachment includes a molecular probe, such as biotin. Other variations of the functionalized attachment are also possible, such as a protein binding ligands, molecules with specific functional groups, and others. The functionalized attachment may be used to determine the attractive interaction between the functionalized attachment and the sample surface. Those and other variations are possible.

Figure 2:
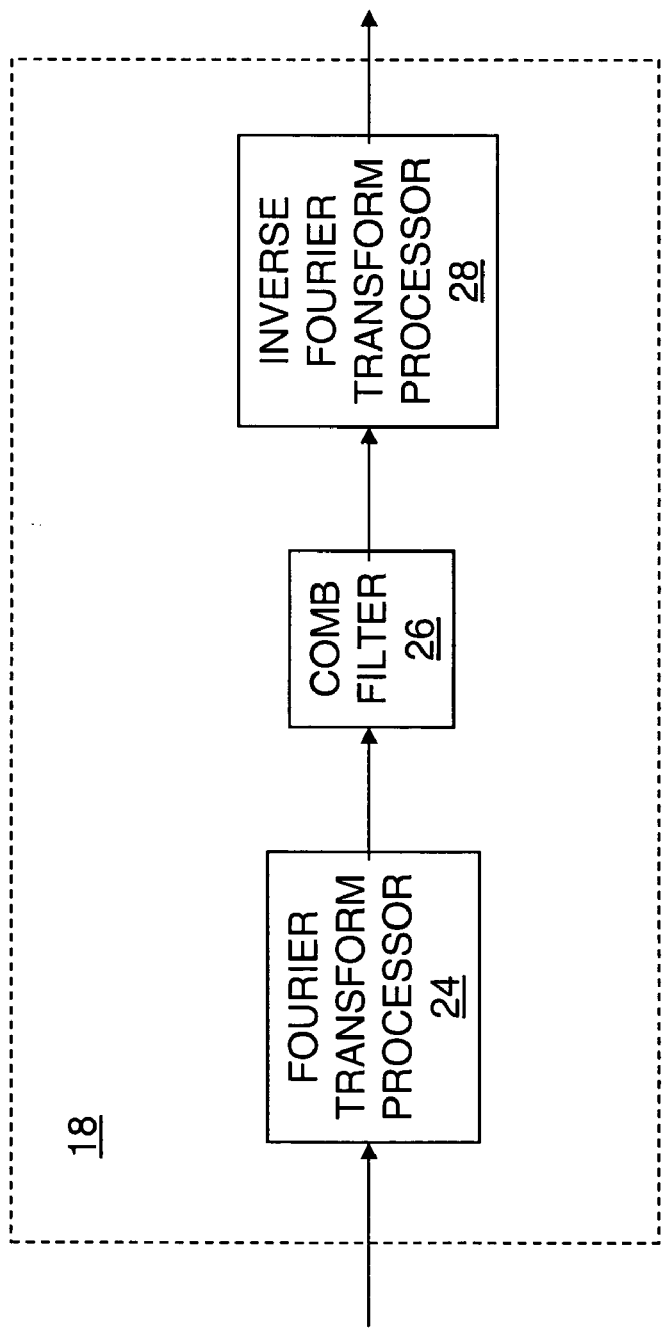
FIG. 2 illustrates one embodiment of a filter 18 according to the present invention.

FIG. 2 illustrates one embodiment of a filter 18 according to the present invention. In that embodiment, the filter 18 includes a Fourier transform signal processor 24, a comb filter 26, and an inverse Fourier transform signal processor 28. Alternatively, a single signal processor may be used to perform all of the functions of processor 24, comb filter 26, and processor 28. In some embodiments, more than two signal processors may be used. In other embodiments, the Fourier transform signal processor 24, the comb filter 26, and the inverse Fourier transform signal processor 28 may be implemented in hardware, or as a combination of hardware and software. Other variations are also possible.

Figure 3:
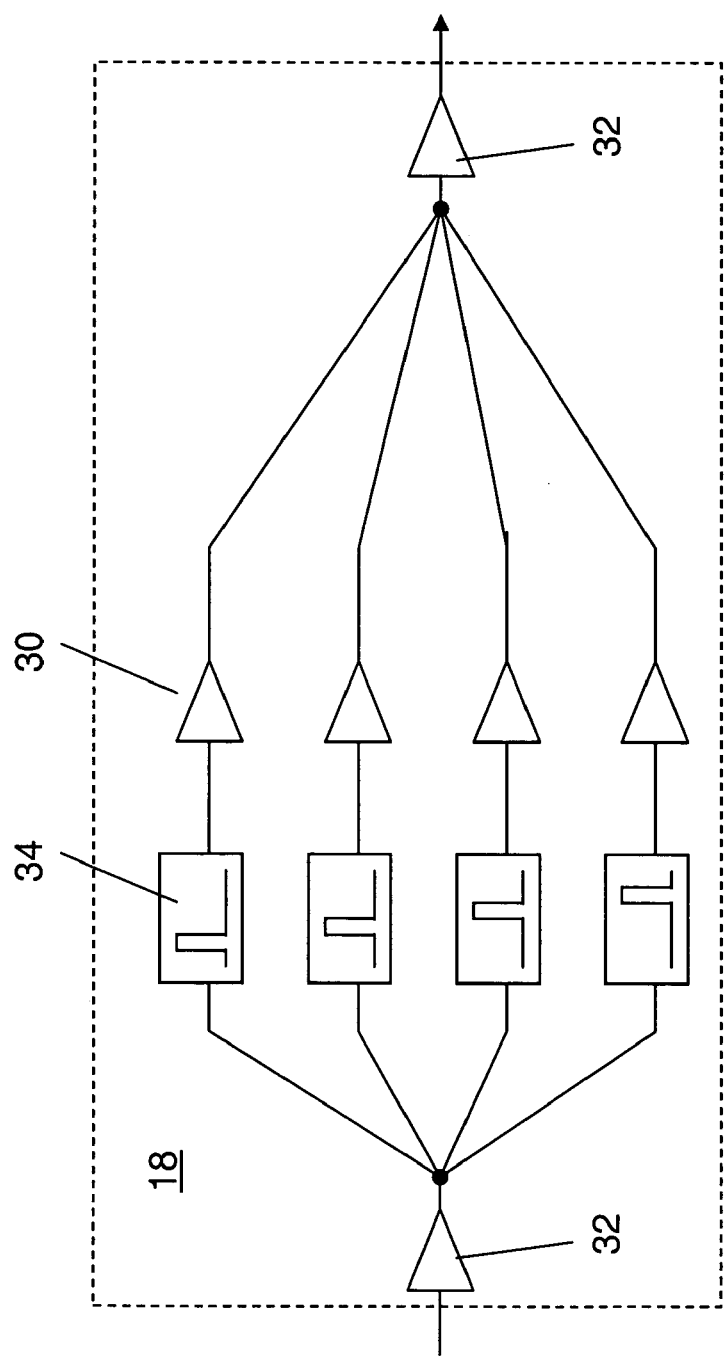
FIG. 3 illustrates another embodiment of a filter 18 according to the present invention.

FIG. 3 illustrates another embodiment of a filter 18 according to the present invention. In that embodiment, frequency-specific amplifiers 30 are used to filter the deflection signal from the proximal probe 10. The deflection signal is split to each amplifier 30 and combined after passing through the amplifiers 30. In the illustrated embodiment the frequency-specific amplifiers 30 each correspond to a harmonic of the resonant frequency of the cantilever or probe 12 and collectively the frequency-specific amplifiers 30 act as a comb filter for the desired frequencies of the deflection signal. Alternatively, the amplifiers 30 may correspond to other desired frequencies. Although four frequency-specific amplifiers 30 are illustrated, more or less lock-in amplifiers 30 may be used.

The frequency-specific amplifiers 30 may be, for example, lock-in amplifiers. Other variations are also possible. For example, the amplifiers 30 themselves may not be frequency-sensitive, but they may be coupled to band-pass or other filters 34 to allow for frequency-selective amplification of the deflection signal. In addition, other components may also be includes. For example, the deflection signal may be amplified before and/or after the amplifiers 30. In addition, additional signal filters 34 may be used before and/or after the amplifiers 30. In another embodiment, band-pass filters 34 are used with lock-in amplifiers 30 so as to pass only signals near the frequency to be amplified by the corresponding lock-in amplifier 30.

Figure 4:
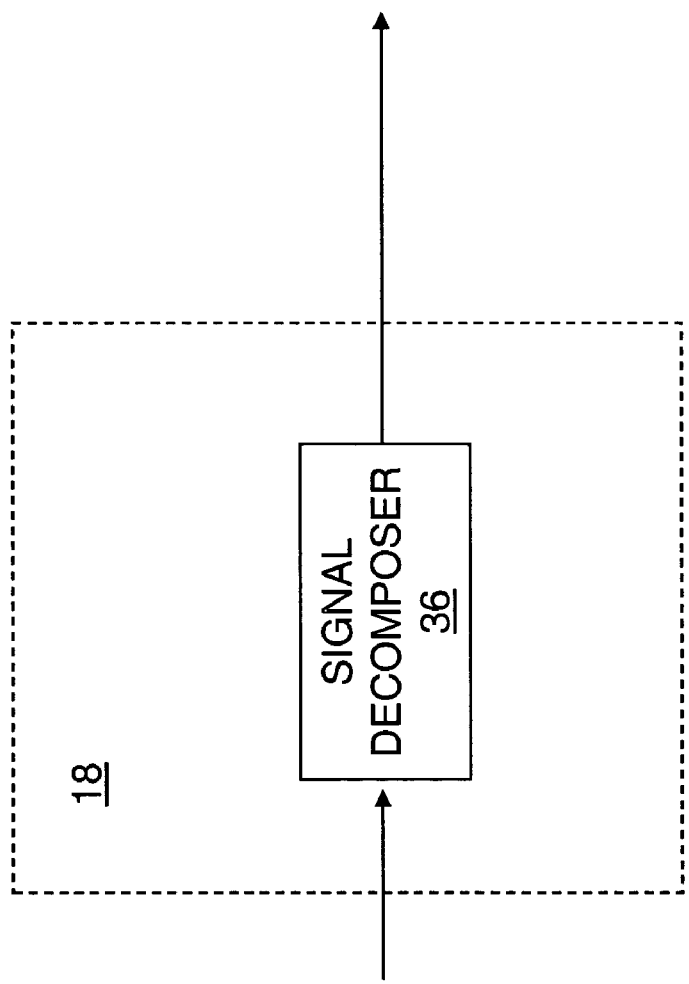
FIG. 4 illustrates another embodiment of a filter 18 according to the present invention.

FIG. 4 illustrates another embodiment of a filter 18 according to the present invention. In that embodiment, the filter 18 includes a signal decomposer 36. The signal decomposer 36 may be implemented, for example, as one or more processors including computer readable instructions which, when executed, cause the signals to be processed in a particular manner. In other embodiments, the signal decomposer 36 may be implemented in hardware or in a combination of hardware and software.

The present invention also includes methods for operating proximal probes such as scanning probe microscopy and related methods. One embodiment of the present invention is a method of extracting time-resolved tip/sample forces from tapping mode atomic force microscopy (TMAFM) experiments based on the second derivative of the cantilever or probe 12 deflection signal. The methods according to the present invention may be implemented, for example, with the apparatuses described hereinabove, and with variations and modifications of those apparatuses. The methods of the present invention will be described via both numerical simulations and experiments. Examples of operation of the present invention will use samples of lipid bilayers on mica. Supported lipid bilayer patches on mica were chosen to illustrate the operation of the present invention because of the change in surface modulus between the bilayer patch and mica offers an opportunity to compare tip-surface force interactions on different surfaces. However, the present invention may also be used with other surface samples and materials.

In an effort to more fully understand the interaction between the tip of the probe 12 and the sample in TMAFM, numeric simulations are often used that describe the motion of a cantilever as a driven, damped harmonic oscillator:

$$m_{eff}\ddot{z}+b\dot{z}+k[z-D_0+a_0\sin(\omega t)]=F_{ext} \quad (1)$$

where $m_{eff}$ is the effective mass of a cantilever, b is the damping coefficient, k is the cantilever spring constant, $a_0$ is the drive amplitude, $\omega$ is the drive frequency, $D_0$ is the resting position of the cantilever base, $F_{ext}$ is the tip-sample force, and z is the position of the cantilever with respect to the surface. In practice, it is the deflection of the cantilever that is monitored in AFM experiments. The difference between the position and deflection signal is minimal for high Q systems; however, these signals are drastically different in low Q systems such as fluid tapping AFM. The deflection (y) is given by:

$$y=z-D_0+a_0\sin(\omega t) \quad (2)$$

and Equation 1 can be re-written as:

$$m_{eff}[\ddot{y}-a_0\omega^2\sin(\omega t)]+b[\dot{y}+a_0\omega\cos(\omega t)]+ky=F_{ext} \quad (3)$$

Rearranging Equation 3, it can be shown that the tip acceleration can be decomposed into a pulse-like tip-sample force ($F_{ext}$) and other slowly varying terms oscillating at a frequency $\omega$:

$$\ddot{y}=\frac{1}{m_{eff}}\left[F_{ext}-b\dot{y}-ky+m_{eff}\omega^2 a_0\left[\sin(\omega t)+\frac{1}{Q}\cos(\omega t)\right]\right] \quad (4)$$

Thus, the contribution due to the time resolved tip sample force can be distinguished from other terms in the second derivative of the cantilever deflection signal, providing a simple method to reconstruct the tapping force. A problem in reconstructing the tapping force is the noise in the deflection signal. According to the present invention, the noise can be effectively suppressed through comb filtering based on higher harmonics as well as with other variations and embodiments of the present invention. This approach is made possible by the fact that higher harmonics contain virtually complete information about the anharmonic part of the cantilever deflection trajectory. The comb filter 26, as described hereinabove, is used to extract harmonics from the Fourier transform of the deflection signal, and an inverse Fourier transform is calculated to give the filtered deflection trajectory. This application of the present invention will sometimes be referred to as scanning probe acceleration microscopy (SPAM) and it can make use of the entire cantilever deflection trajectory to map local forces in a time resolved manner.

Figure 5:
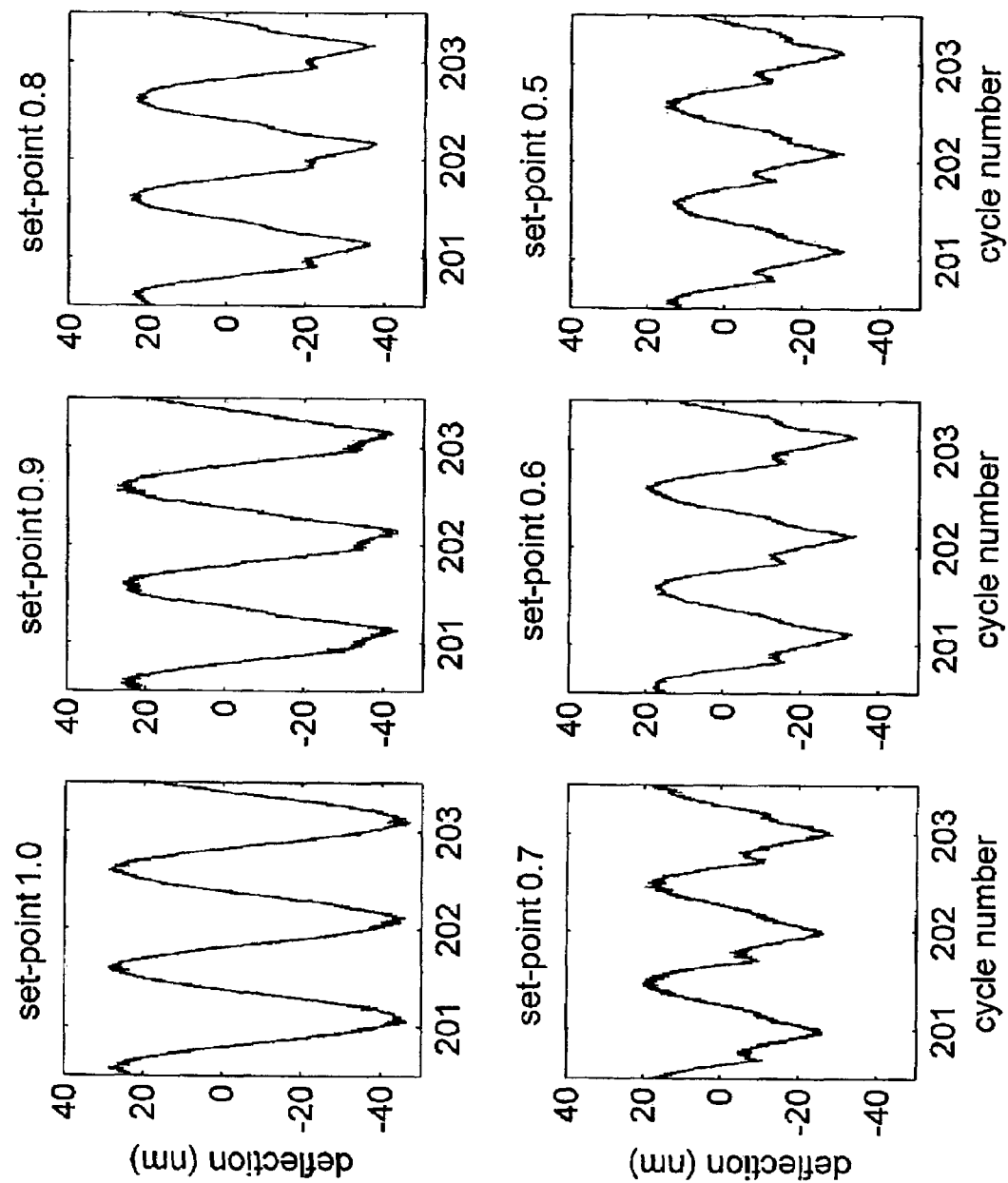
FIG. 5 illustrates cantilever deflection trajectories taken from actual fluid tapping mode AFM experiments as a function of set-point.

FIG. 5 illustrates cantilever deflection trajectories taken from actual fluid tapping mode AFM experiments as a function of set-point. The deflection trajectories are characterized by a large, anharmonic motion of the cantilever that becomes more pronounced with deeper values of set-point. The ability of the comb filter 26 to accurately reconstruct the deflection trajectory is dependent on the number of harmonics that appear above the noise level of the Fourier transform. In general, the more harmonics that are captured, the more accurate the reconstructed deflection trajectory. As will be shown by simulation, this large distortion of the trajectory in fluid TMAFM can be directly related to the low quality factor (Q) of the cantilever due to the viscous damping in the fluid. Herein, we show that for such highly anharmonic signals found in fluid TMAFM the tip-sample tapping force can be relatively easily reconstructed from the second derivative (or acceleration) of the cantilever deflection signal because the large number of higher harmonics excited by the highly anharmonic motion make comb-filtering feasible. Tapping force can be directly related to material properties of the surface, and in particular to the surface modulus. The use of SPAM is illustrated through both numerical simulations and experiments.

The present invention will be described in terms of both simulations and experiments. For the experiments, total brain lipid extract was purchased from Avanti Polar Lipids, dried under a stream of nitrogen, lyophilized, and resuspended in PBS (pH 7.3) at a concentration of 1 mg/ml. By using an acetone dry-ice bath, bilayers and multilayer lipid sheets were formed by five sequential freeze-thaw cycles. The lipid suspensions then were sonicated for 15 min to promote vesicle formation. Then 40 µl of the suspended vesicle solution diluted five times was added directly to the AFM fluid cell by using the hanging drop method and placed on freshly cleaved mica, allowing the vesicles to flatten and fuse in situ. In situ AFM experiments were performed with a Nanoscope III MultiMode scanning probe microscope (Digital Instruments, Santa Barbara, Calif.) by using a tapping fluid cell equipped with an O-ring and a V-shaped oxide-sharpened silicon nitride cantilever with a nominal spring constant of 0.5 N/m. Images were acquired with a "vertical engage" J-scanner. Scan rates were set at 1-2 lines per second with cantilever drive frequencies ranging from ~8 to 10 kHz, and 5*1.25 µm images were captured at 256*64-pixel resolution. Cantilever deflection trajectories were simultaneously captured through an AFM signal access module (Digital Instruments) by using a CompuScope 14100 data acquisition card (Gage Applied Technologies, Lachine, QB, Canada). Trajectories were captured at 5-10 MS/s and 14-bit resolution.

EXAMPLE 1

Simulation Demonstrates the Applicability of SPAM Analysis in Fluids

Numerical simulations were performed with Simulink and Matlab (MathWorks Inc., Natick, Mass.) using a single degree of freedom model of tapping mode AFM cantilever based on Equation 1. When the tip-sample separation distance z from the surface is large enough, the tip never touches the surface, and the external force can be approximated using a well-known expression for the van der Waals interaction between a sphere and a flat surface:

$$F_{ext} = -HR_{tip}/6z^2 \quad (5)$$

where H is the Hamaker constant and $R_{tip}$ is the tip radius. With the decrease of distance $D_0$, the tip eventually begins to strike the surface at the bottom of each oscillation cycle. Under these circumstances, the tip-sample force can be described using the Derjaguin-Muller-Toporov (DMT) model:

$$F_{ext} = 4/(3\pi\kappa_{eff})\sqrt{R_{tip}}(a_{DMT}-z)^{3/2} - HRtip/6a_{DMT}^2 \quad (6)$$

where $a_{DMT}$ is the intermolecular distance parameter of DMT potential, and $\kappa_{eff} = (1-v_1^2)/(\pi E_1) + (1-v_2^2)/(\pi E_2)$ where $E_1$, $v_1$ and $E_2$, $v_2$ are respectively the Young's modulus and Poisson coefficient of the tip and the sample. The surface charge densities for mica and silicon nitride used in the simulation were equal to −0.0025 and −0.032 C/m², respectively. The model step used in simulations was five nm tall with variable surface modulus on the step and 60 GPa elsewhere.

Steps formed by bilayer patches on mica were simulated with a surface modulus of 1 GPa. In addition, the equations for $F_{ext}$ may be further modified to include other forces. For example, for operation in an electrolyte fluid, $F_{ext}$ may be calculated as:

$$Fext = \frac{4\pi\sigma_s\sigma_{tip}R_{tip}\lambda_D}{\varepsilon_e\varepsilon_o}e^{-D/\lambda_D} - \frac{HR_{tip}}{6D^2} \text{ for } D \geq a_{DMT} \quad (7)$$

where $\sigma_S$ and $\sigma_{tip}$ are the surface charge densities of sample and tip, $\in_o$ is the permittivity of vacuum, $\in_c$ is the dielectric constant of the medium, and $\lambda_D$ is the Debye length ($\lambda_D=0.304/e_c$ for monovalent electrolytes with $e_c$ being the electrolyte concentration). Other terms may also be added or substituted, such as to represent magnetic forces or other forces.

Single degree of freedom simulations of tapping mode AFM in fluids were performed with parameters based on actual AFM experiments to be described later. Typical conditions used in simulations of fluid TMAFM were as follows: resonance frequency of 8 kHz (with operating frequencies slightly above resonance), k of 0.5 N/m, Q of 2, and cantilever free amplitude of 40-75 nm. The model was equipped with a feedback loop (integral gain) that allowed for the simulation of imaging operation. The free amplitude for these simulations was set to $A_0=75$ nm to more closely correspond to actual experiments, and using an integral gain, the tapping amplitude was maintained at 75% of the free amplitude (set-point ratio of $A/A_0=0.75$). As discussed earlier, the anharmonicity of fluid TMAFM deflection trajectories is manifested by a characteristic pronounced distortion (FIG. 5).

Figure 6:
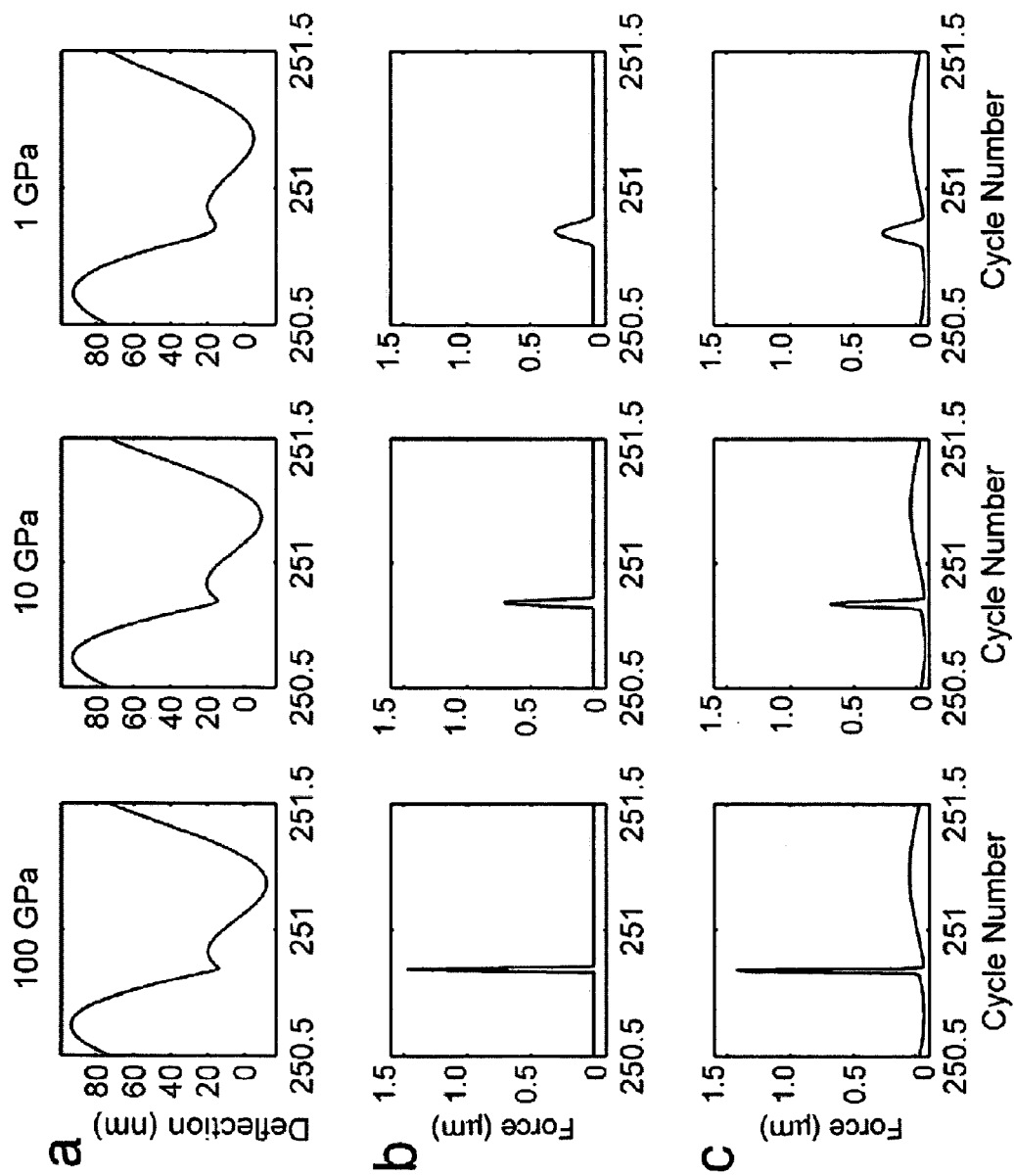
FIG. 6 illustrates simulated fluid tapping mode AFM experiments on various surfaces.

FIG. 6 illustrates simulated fluid tapping mode AFM experiments on surfaces with Young's moduli of 100, 10, and 1 GPa. FIG. 6a illustrates resulting cantilever deflection signal and FIG. 6b illustrates tip-sample force on different surfaces. The deflection signals display the characteristic anharmonic motion of fluid tapping mode AFM with the degree of anharmonicity decreasing with softer surfaces. However, while the area under the force pulse, or the average force per cycle, remains constant, the maximum tip-sample force decreases with decreasing surface rigidity, and the width of the force spike increases. FIG. 6c illustrates the tip-sample force recovered from the second derivative of the deflection signal, which corresponds to the tip acceleration. Notice that a small sinusoidal oscillation is now superimposed on the force trace. This sinusoidal oscillation can be removed by filtering out the first two harmonics of the Fourier transform, as described hereinbelow.

The simulated AFM experiments were able to reproduce this characteristic shape in the deflection signal (FIG. 6a), and comparison with the tip-sample force plots (FIG. 6b) showed that this distortion coincided with intermittent contact between the tip and sample surface. This characteristic distortion was present in simulated tip-sample interactions with varying surface Young's moduli; with the decrease of surface modulus, the distortion in the deflection signal became less pronounced. FIG. 6b shows also the well known change in tapping force pulse shape with the change in surface modulus: at a constant set-point, the area under the peak remains constant, whereas its width (contact time) increases and height decreases with the decrease of E. The latter dependence of maximum tapping force on sample modulus provides a basis fob SPAM analysis. Based on equation 4, taking the second derivative of the deflection signal and properly scaling by the effective mass of the cantilever results in a recovery of the tip/sample force (FIG. 6c).

Figure 7:
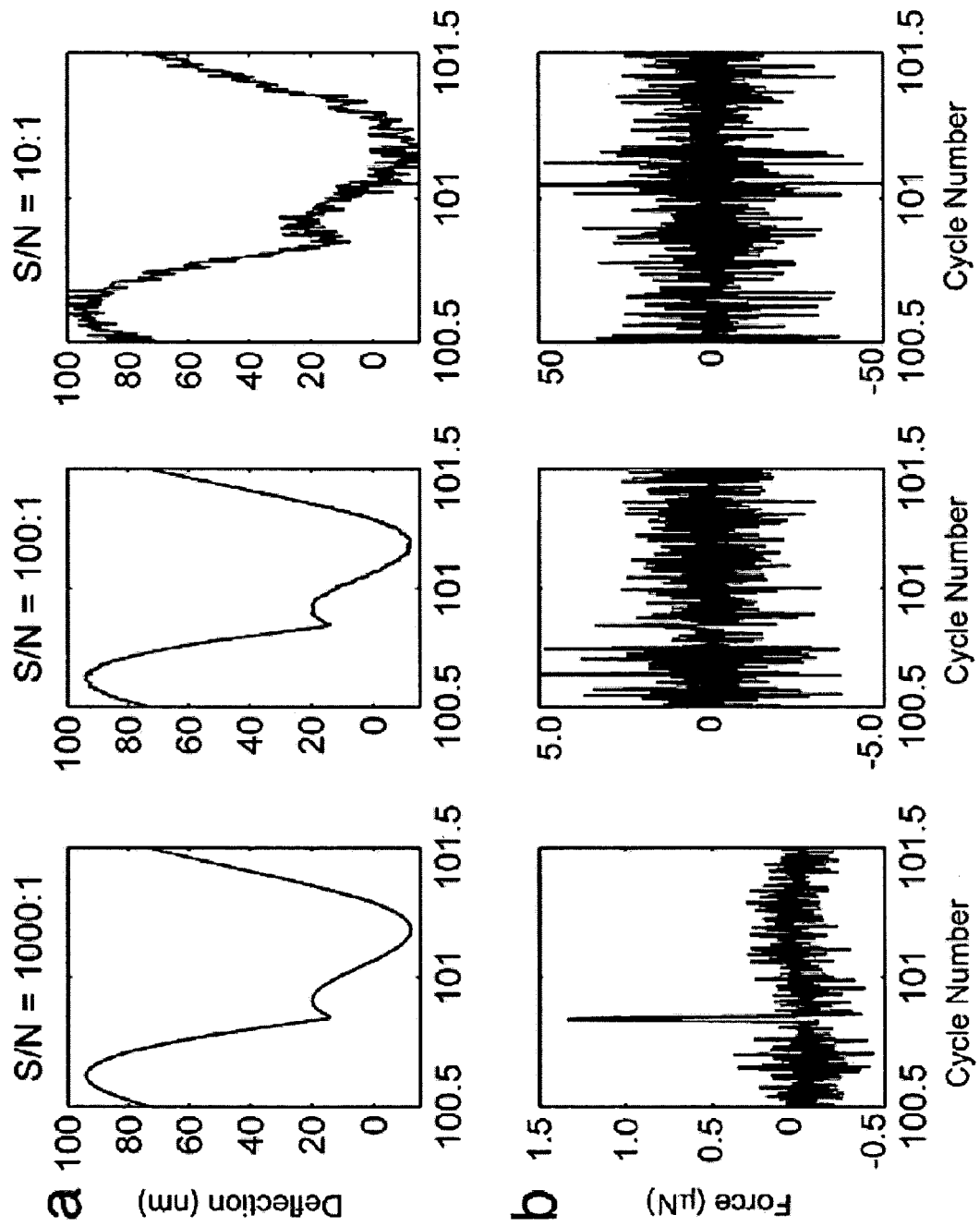
FIG. 7 illustrates the effect of noise in the deflection signal on the force reconstruction from tip acceleration in simulated fluid tapping mode AFM experiments.

FIG. 7 illustrates the effect of noise in the deflection signal on the force reconstruction from tip acceleration in simulated fluid tapping mode AFM experiments. FIG. 7a illustrates deflection signals with S/N ratios of 1000:1, 100:1; and 10:1. FIG. 7b illustrates their respective recovered force interactions. Whereas, the characteristic distortion associated with TMAFM in fluids was still discernible even with S/N ratios reaching 10:1, the derivative of the signal was completely overwhelmed by noise at S/N ratios as low as 100:1. Since S/N levels in typical AFM deflection signals may be of this order (or worse), at least some embodiments of the present invention utilize filtering or signal processing of noisy deflection signals for real systems. The filter must not significantly alter the shape of the distortion in the deflection signal so that the force reconstruction can accurately determine the tip-sample interaction. One embodiment of such a filter is the Fourier transform and harmonic comb filter 26 according to the present invention.

Figure 8:
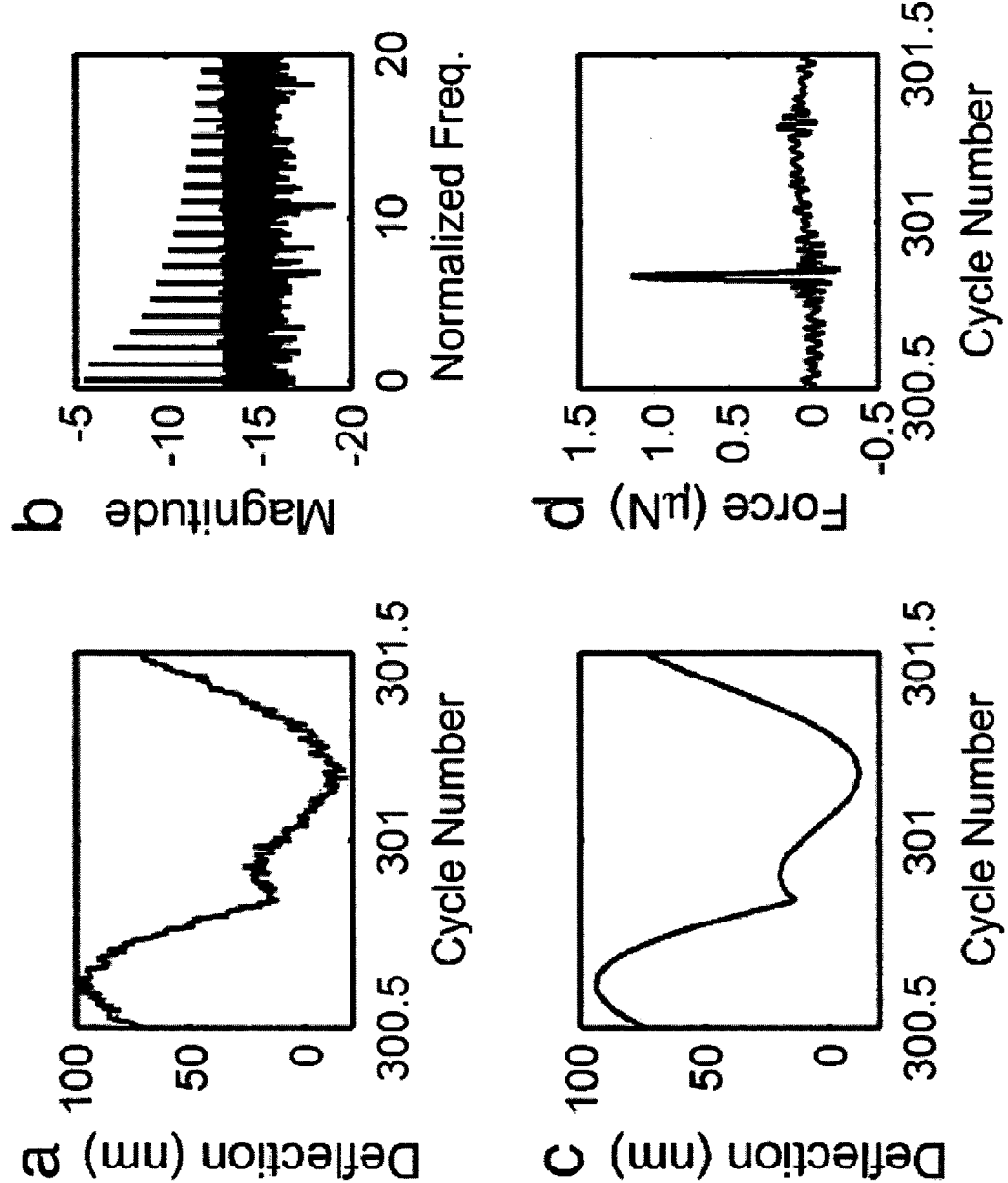
FIG. 8 illustrates the operation of a method according to one embodiment of the present invention utilizing a Fourier transform and a comb filter.

FIG. 8 illustrates the operation of a method according to one embodiment of the present invention utilizing a Fourier transform and a comb filter. FIG. 8a illustrates a simulated deflection signal with a signal to noise ratio of 20:1 and with a fluid tapping mode AFM on a 60 GPa surface. FIG. 8b illustrates the signal in the frequency domain after a Fourier transform. In this example, many harmonics are clearly visible above the noise. A comb filter is applied to the Fourier transform signal with pass bands corresponding to the harmonics and stop bands corresponding to the remainder of the signal. An inverse Fourier transform is applied to the comb filtered signal resulting in a reconstructed deflection signal as illustrated in FIG. 8c. The reconstructed signal illustrated in FIG. 8c has significantly less noise than the original signal illustrated in FIG. 8a. A second derivative is calculated from the reconstructed signal, resulting in the graph illustrated in FIG. 8d. FIG. 8d illustrates the tip-sample force recovered from the filtered and reconstructed deflection signal, which corresponds to the tip acceleration. The largest peak corresponds to the impact of the probe 12 on the sample surface. Because some information is inevitably lost due to harmonics in the noise of the signal, it is expected that the reconstructed force will be of less magnitude than the actual force.

In summary, the Fourier transform of the deflection signal is comb filtered (i.e. only intensities corresponding to integer harmonic frequencies are kept) and the integer harmonic frequencies are used to reconstruct a deflection signal, $y_{rec}(t)$, by inverse Fourier transform based on the following equation:

$$y_{rec}(t) = \mathfrak{S}^{-1}\left[y(\omega)\sum_{k=1}^{N} \delta(\omega - k\omega_{oper})\right] \quad (8)$$

where $\omega_{oper}$ is the operating frequency and $\delta$ is the Dirac's delta function (FIG. 8c). The summation is carried out up to N, which is the highest harmonic still distinguishable above the noise level. Due to the suppression of some harmonics, a portion of the force magnitude is lost in reconstruction as can be seen for example by comparing the peaks in FIG. 6b (the 100 GPa sample) and its reconstructed equivalent shown in FIG. 8d. Despite this loss of information, the reconstructed signal still contains the information allowing one to differentiate between surfaces with different elasticity. The terms in the second derivative that oscillate at the frequency ω are primarily contained in the first two harmonics. By excluding the first two harmonics in the comb-filter 26, this underlying oscillation can be suppressed; however, the trade-off is a loss of magnitude in the reconstructed tapping force trajectory.

FIG. 9 illustrates simulations showing spatially resolved force reconstruction of fluid tapping-mode AFM experiment imaging a soft step on a rigid surface having a rectangular 5 nm step. The Young's modulus of the surface was 60 GPa before and after the step, but it was lower on the step where it could range from 1 GPa to 59 GPa. The simulation parameters were chosen in such a way that they corresponded to imaging a 2.5 μm line with a scan rate of 5 lines/s. In summary, the feedback loop maintained constant cantilever amplitude along the whole trace (with the exception of edges where transients appeared), the average force per cycle remained constant. In contrast, the maximum value of tapping force and the width of the force pulse varied when the cantilever passed over the regions of different Young's modulus (FIG. 9b). These changes in force could also be completely recovered from the second derivative of the deflection signal (FIG. 9c).

Figure 9A:
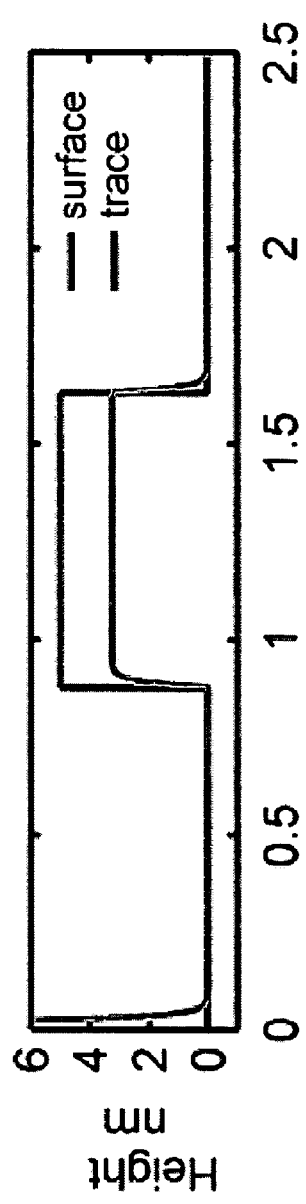
FIG. 9 illustrates simulations showing spatially resolved force reconstruction of fluid tapping-mode AFM experiment imaging a soft step on a rigid surface having a rectangular 5 nm step.

FIG. 9a illustrates the actual surface topography and the surface trace acquired via an AFM simulation using a feedback loop equipped with an integral gain. In this simulation, the surface modulus is 60 GPa before and after the step, and 1 GPa on the step. This simulation is equivalent to scanning a line 2.5 μm in length at a rate of 5 lines/s with a set-point of 75% of free amplitude. The AFM trace of the step is smaller in height than the simulated surface due to compression of the soft step by the tapping force. On the edges of the step, it can be seen that the feedback loop has a finite response time.

Figure 9B:
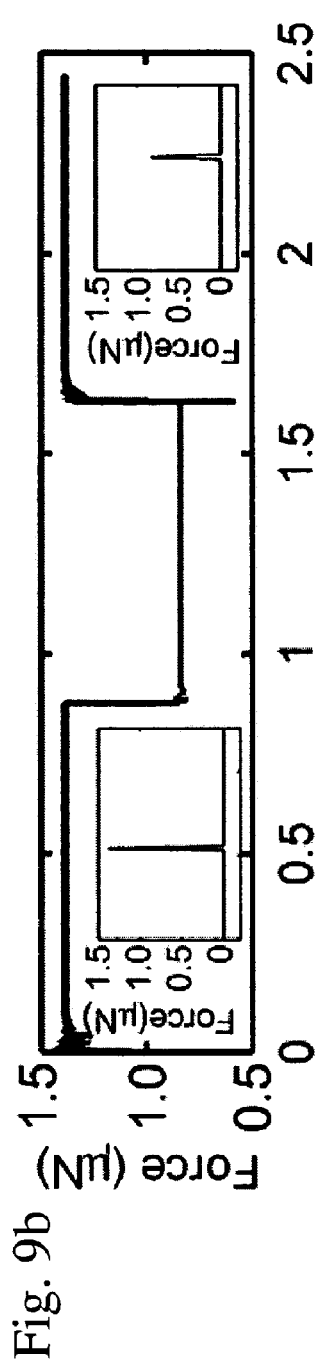

FIG. 9b illustrates the actual spatially resolved tapping force recovered from the simulation shows that the maximum tapping force changes in response to the shift in surface modulus over the step. The force pulse corresponding to tapping events on the more rigid areas (inset on the left) of the simulated surface has a larger maximum value and is sharper when compared to the force pulse on the softer step (inset on the right).

Figure 9C:
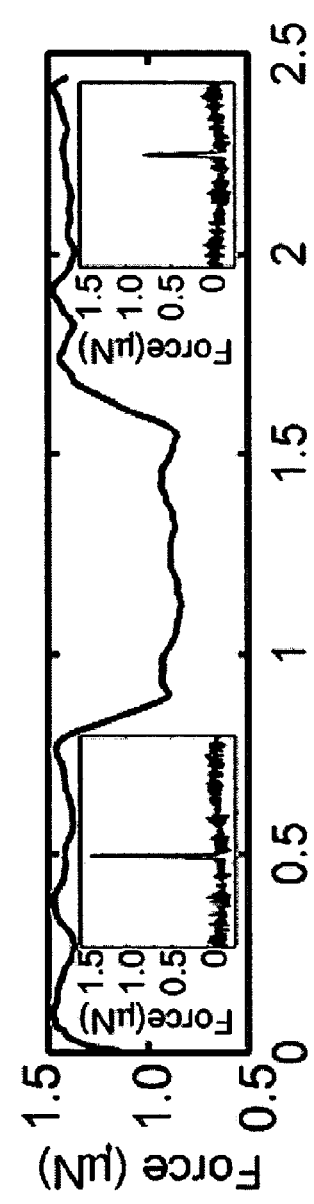

FIG. 9c illustrates a noisy (S/N=20:1) simulated deflection trajectory was comb-filtered and used to reconstruct the force interaction. It was necessary to use a sliding window Fourier transform to maintain the local character of the deflection trajectory. Again, the qualitative differences between force pulses on rigid (inset on the left) and soft (inset on the right) surface areas are distinguishable.

Figure 9D:
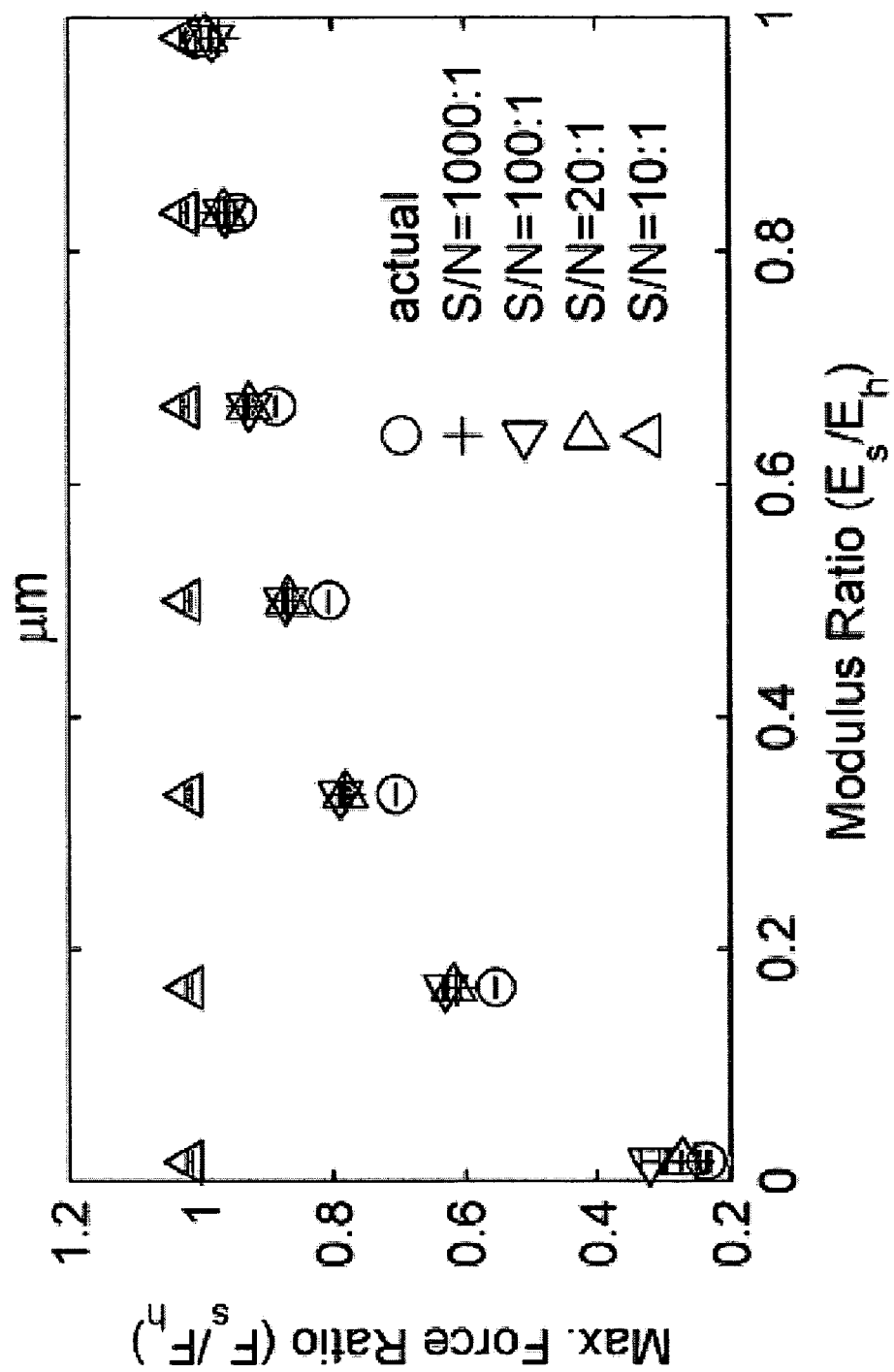

FIG. 9d illustrates the ratio of the maximum force on soft and hard areas of the surface was plotted versus the ratio of the soft and hard Young's modulus. Such a curve can be used as a calibration to extract relative values of surface modulus. With the application of harmonic comb-filtering, it was still possible to reproduce the relationship between the ratio of maximum forces for different ratios of Young's modulus from deflection trajectories with S/N ratios as low as 20:1.

Figure 10:
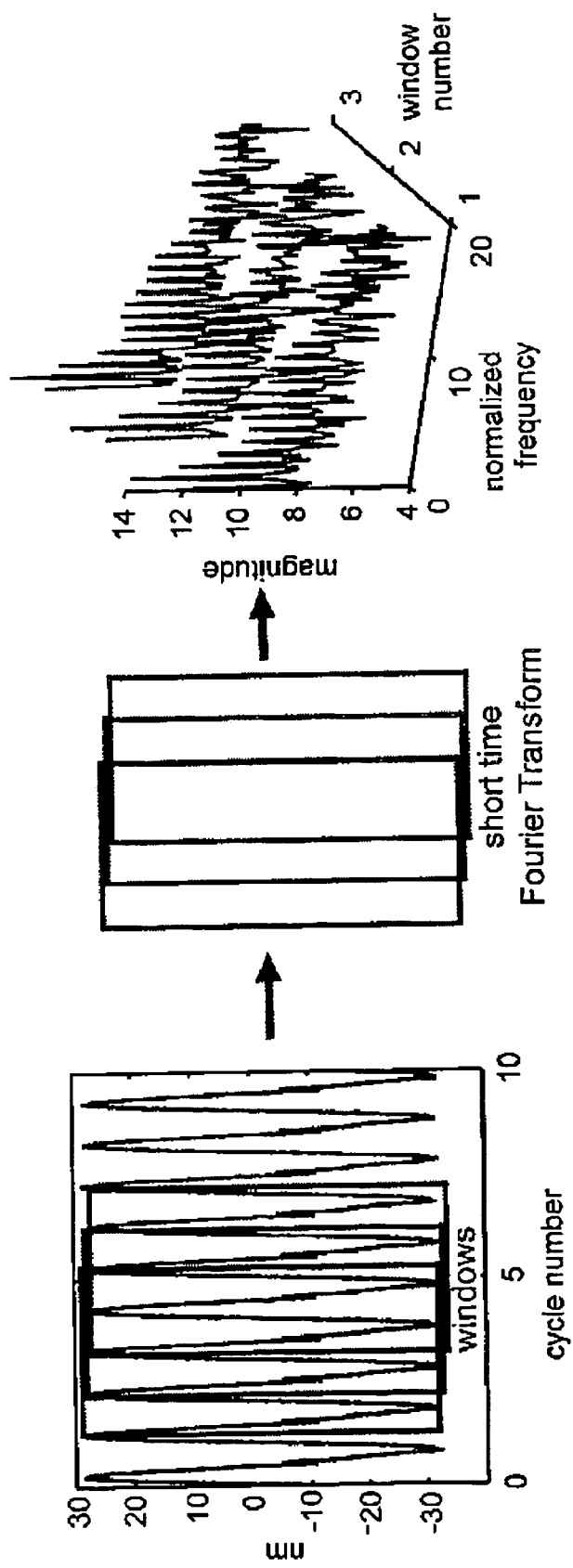
FIG. 10 illustrates the use of a sliding window Fourier transform used on a cantilever deflection signal.

FIG. 10 illustrates the use of a sliding window Fourier transform used on a cantilever deflection signal. This was done to accurately reproduce local changes in the deflection signals, such as transients associated with step edges. This sliding window Fourier transform was performed over 5 cycles with an overlap of 4 cycles between slices of the trajectory. With the application of harmonic comb-filtering, it was still possible to reproduce the relationship between the ratio of maximum forces for different ratios of Young's modulus from deflection trajectories with S/N ratios as low as 20:1 (FIG. 9d).

EXAMPLE 2

Application of SPAM in Differentiating Between Surface Properties in Fluids

Figure 11:
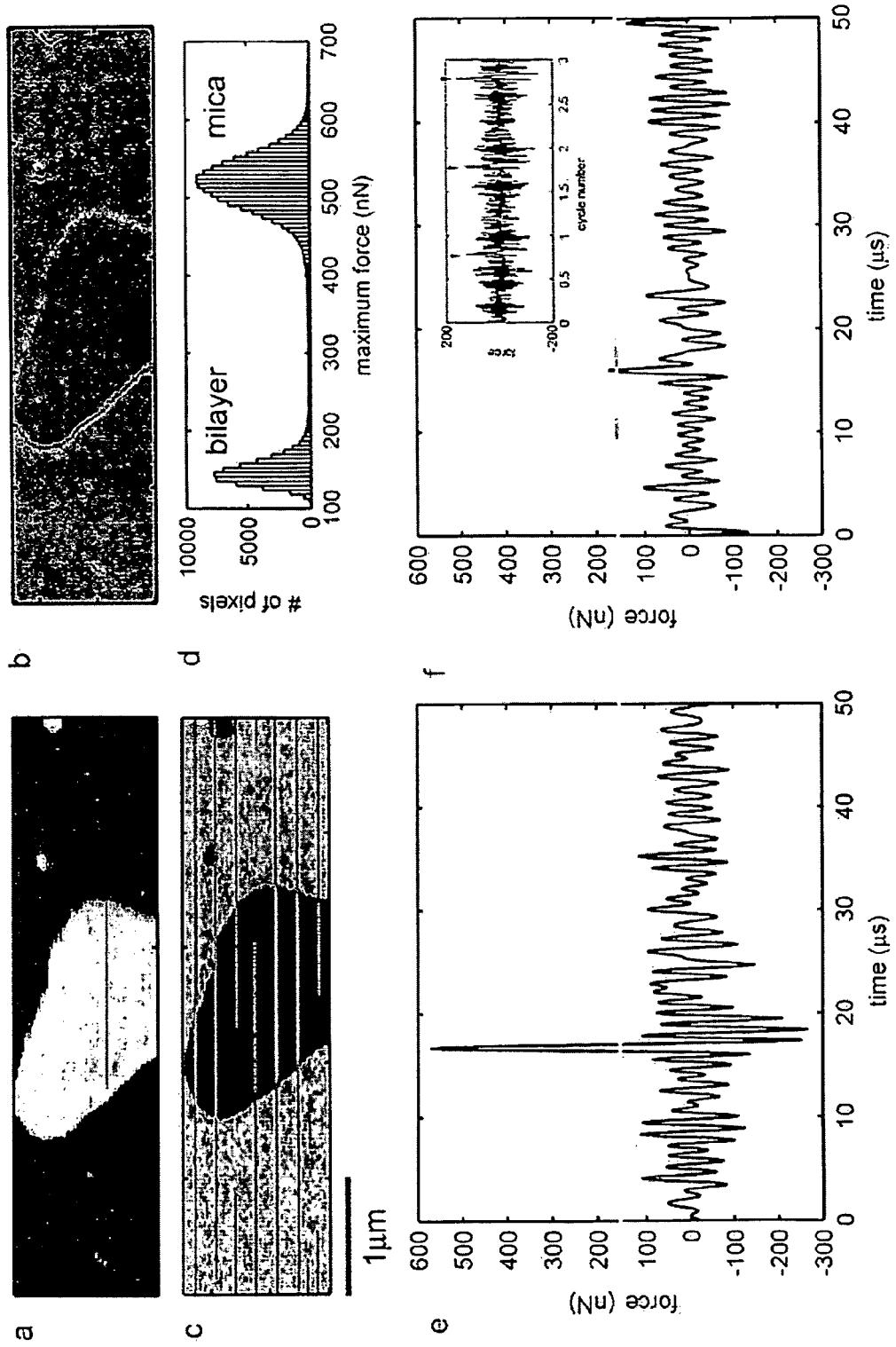
FIG. 11 illustrates a series of fluid tapping mode AFM images of a supported brain lipid extract bilayer on mica demonstrating the use of higher harmonics in imaging and the ability to spatially resolve the tapping force.

FIG. 11 illustrates a series of fluid tapping mode AFM images of a supported brain lipid extract bilayer on mica demonstrating the use of higher harmonics in imaging and the ability to spatially resolve the tapping force. Exposed mica is clearly seen in standard height (FIG. 11a) and amplitude (FIG. 11b) images as well as the maximum force map (FIG. 11c) acquired from the AFM experiment. FIG. 11d illustrates a histogram of the maximum tapping forces from an image of a bilayer on a mica surface. Two Gaussian distributions of maximum tapping force are clearly resolved from each other that correspond to the soft bilayer and the rigid mica surface, demonstrating that relative elastic properties of the sample can be spatially resolved using the present invention. The use of a sliding window Fourier transform comb-filter to reconstruct a noisy real deflection signal of a fluid tapping-mode AFM experiment is demonstrated on mica (FIG. 11e) and bilayer (FIG. 11f). Comparisons between the reconstructed force pulses associated with a single tapping event on mica and a bilayer patch demonstrate the effectiveness of the present invention to distinguish between the two areas of differing modulus, and the characteristic changes in the force pulses as predicted by simulation were apparent. The inset in FIG. 11f shows the force trajectory over a bilayer for three cycles, with each tapping event indicated by an arrow.

The bilayer patches on mica were imaged using fluid TMAFM while the entire cantilever deflection trajectory was digitized. As can be seen in FIG. 11, contrast was observed in both height and amplitude. These cantilever deflection trajectories were comb-filtered and the entire maximum force map of the surface was reconstructed (FIG. 11c), with darker colors corresponding to lower values of maximum tapping force. Due to limitations in the memory of the data acquisition card, the deflection trajectory was collected in time stamped portions that later had to be merged and reshaped into an appropriately sized matrix corresponding to the AFM image. Due to the latency associated with flushing the card memory, small portions of the cantilever deflection trajectory were missing, and the resulting gaps were manifested as horizontal lines in the maximum force image. A histogram of maximum tapping force at each point in the reconstructed force image (FIG. 11d) consists of two distinct Gaussian distributions corresponding to the mica and bilayer surfaces. Consistent with simulation results, the Gaussian distribution of maximum tapping force on the bilayer was shifted toward lower forces in comparison with the distribution of maximum force on mica. Taking the ratio of maximum forces on bilayer to mica, assuming that mica has a Young's modulus of 60 GPa, and using the simulated calibration curve in FIG. 9d, one can estimate the Young's modulus of the bilayer to be of the order of 1-3 GPa.

The deflection signal had a signal to noise ratio of ~50:1, resulting in the necessity of Fourier transform comb filtering. Importantly, even at this S/N level, due to the low Q of the system, up to 50 harmonics were above the noise level, facilitating satisfactory reconstruction. As shown in FIGS. 11e and 11f, SPAM analysis was successful in reconstructing the time-resolved force interaction over both surfaces, and the characteristic force pulses in traces recorded over mica and bilayers differed as predicted by simulations. Since the bilayer (E~1-3 GPa) is much softer than the mica (E~60 GPa) surface, the tapping force spikes on mica (FIG. 11e) were taller and narrower than force spikes on the bilayer (FIG. 11f). It is important to note that due to the limited number of harmonics retained in filtering, the magnitude of the observed forces is smaller than the actual magnitude of the tip-sample force. However, relative comparisons can still be made between the mica and bilayer surfaces since the number of harmonics used in filtering was constant.

Figure 12:
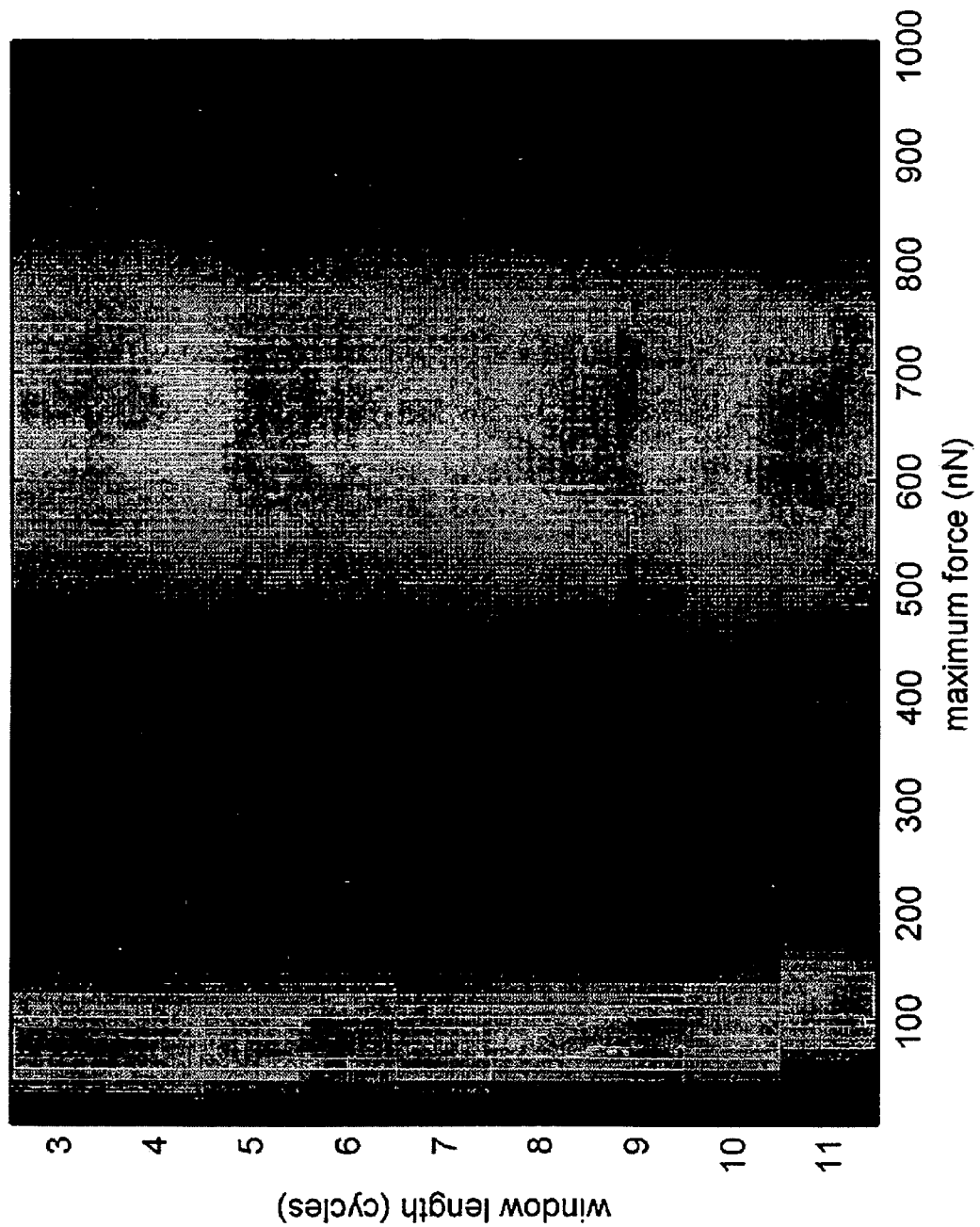
FIG. 12 illustrates a graph showing that contrast in the maximum tapping force is dependent on the window length used in the sliding Fourier transform for comb-filtering.

In order to explore the role of sliding window size, the same image was processed with various windows lengths (measured in oscillation cycles). FIG. 12 illustrates that contrast in the maximum tapping force is dependent on the window length used in the sliding Fourier transform for comb-filtering. As the window length is increased, the value of the maximum force peaks in the histograms decrease or move closer together. This dependence on window length is due primarily to averaging over more cycles with larger windows.

Simultaneous mapping of sample topography and properties is one of the particularly attractive features of proximal probe-based microscopies. Accomplishing this feat is, however, quite challenging. In the very popular tapping mode AFM, it is further complicated by the fact that, in an attempt to minimize the invasiveness of the imaging process, the tip/sample interaction is limited to a very brief encounter when the probe strikes the surface near the bottom of each oscillation cycle. However, according to the present invention information about the tip/sample force interaction can be obtained from cantilever deflection trajectories by taking advantage of the fact that much of the information concerning this interaction is stored in higher harmonics, making it possible to filter and analyze noisy deflection signals to reconstruct the time-resolved tip/sample tapping force. With this ability, spatially resolved force maps can be constructed.

Spatially resolved force maps of a surface can be directly correlated to material properties such as modulus and adhesion. Such force maps can be obtained in so called force volume imaging, which takes a force curve at every point in an AFM image; however, this method is limited by slow scan rates as it can take as long as several hours to obtain one image. In contrast, the force map shown in FIG. 11c was obtained in less than a minute. Studying elastic properties of surfaces by force mapping will allow for the unambiguous assignment of observed surface domains of samples such as phase separated polymer films. This ability could allow for the time-resolved monitoring of changes of nanoscale surface properties under various conditions such as temperature and pH. Since this technique is especially useful in fluid TMAFM due to the particularly pronounced distortion of cantilever trajectory resulting in a large number of harmonics needed for comb-filtering, it has significant potential in biological applications. For example, changes in the modulus of bilayers, cells, and other biological surfaces under the influence of external factors (cholesterol content, structure modifying drugs, etc) could be easily studied.

EXAMPLE 3

Application of SPAM in Studying Changes in Surface Properties in Fluids

A function ascribed to cholesterol residing in bilayer membranes is to alter acyl chain mobility, and the net effect of cholesterol on bilayer fluidity varies based on the lipid composition and temperature. At the lipid content and concentrations commonly found in eukaryotic plasma membranes, the effect of cholesterol is usually to make the membrane more rigid. With the knowledge that lipoprotiens exposed to bilayers swelled most likely due to cholesterol uptake, it is reasonable to predict that the mechanical properties of the bilayers would also change. TBLE bilayers contain a large percentage of cholesterol, and removal of this cholesterol from the bilayer would alter their fluidity. To explore this possibility the present invention was employed to determine if lipoproteins could alter the fluidity of TBLE bilayers. Using the relative value of maximum tapping force, force maps were constructed for bilayer patches on mica before and two hours after treatment with both lipoproteins containing apoE3 and apoE4

Figure 13:
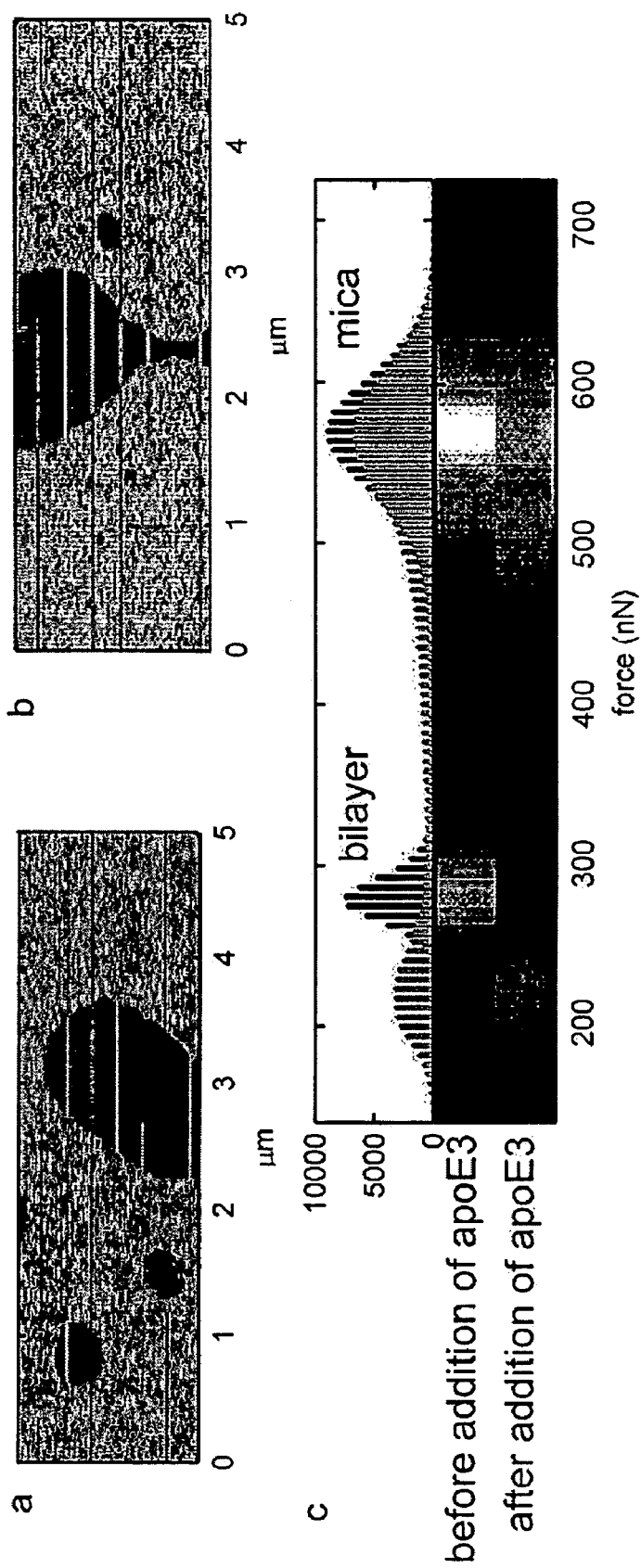
FIG. 13 illustrates an analysis of bilayer patches using the present invention before and after exposure to apoE3-containing lipoprotein particles.

FIG. 13 illustrates an analysis of bilayer patches using the present invention before and after exposure to apoE3-containing lipoprotein particles. Maximum tapping mode force maps of supported bilayer patches on mica before (FIG. 13a) and after (FIG. 13b) the addition of apoE3. FIG. 13c illustrates histograms of maximum tapping forces contain two characteristic distributions corresponding to the mica and bilayer surfaces. After the addition of apeE3, the maximum force on the bilayer decreases, indicating that the bilayer softened in the presences of apoE3.

Figure 14:
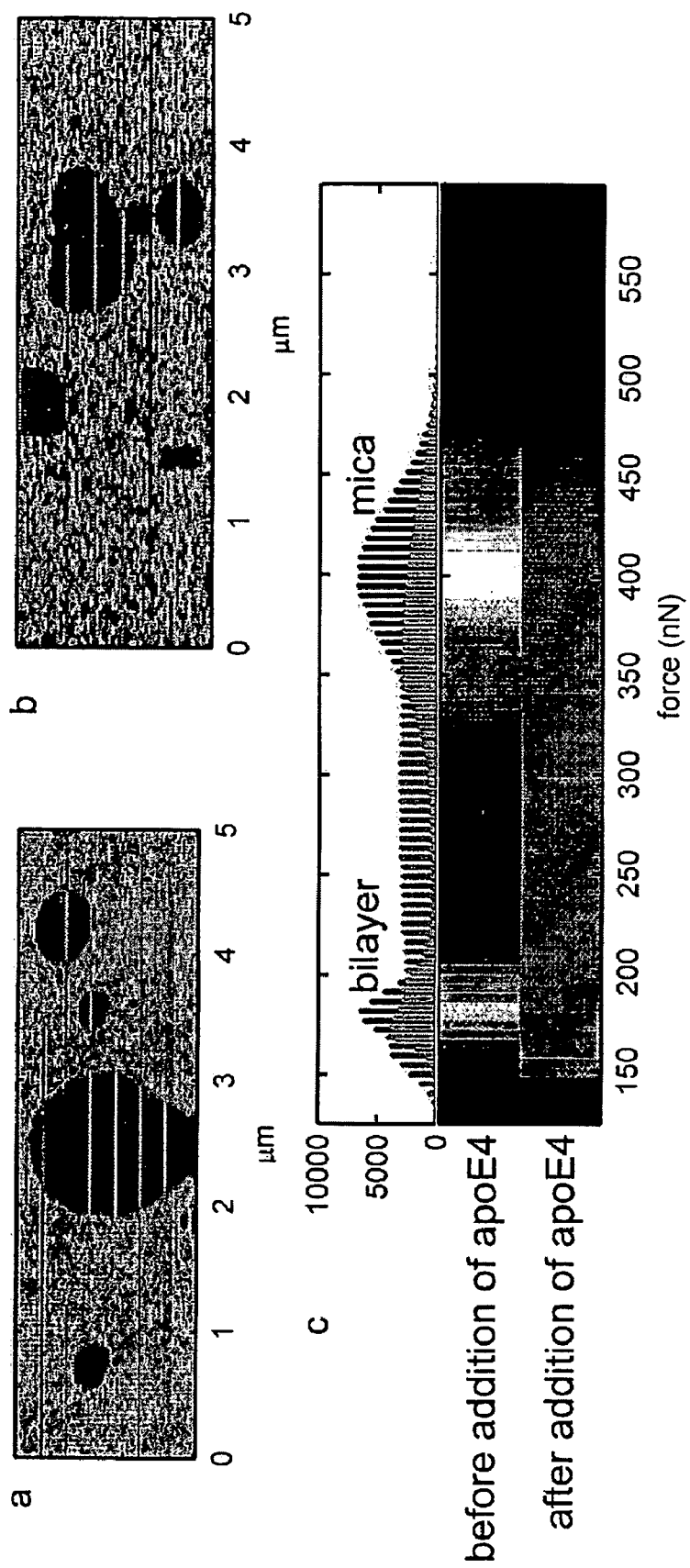
FIG. 14 illustrates an analysis of bilayer patches before and after exposure to apoE4-containing lipoprotein particles.

FIG. 14 illustrates an analysis of bilayer patches before and after exposure to apoE4-containing lipoprotein particles. Maximum tapping mode force maps of supported bilayer patches on mica before (FIG. 14a) and after (FIG. 14b) the addition of apoE4. FIG. 14c illustrates histograms of maximum tapping forces contain two characteristic distributions corresponding to the mica and bilayer surfaces. After the addition of apoE4, the maximum force on the bilayer decreases, indicating that the bilayer stoftened in the presences of apoE4. However, this shift is less pronounced when compared to the shift in the presence of apoE3.

The histograms reveal that the maximum tapping force associated with the bilayer decreased after the addition of the lipoproteins (FIGS. 13c and 14c). In such experiments, the maximum tapping force associated with the mica substrate acts as an internal control. This smaller force represents a softening of the bilayer or an increase in fluidity. This indirectly supports the notion that lipoproteins are extracting cholesterol from the bilayers, as removal of cholesterol is a known mechanism to alter bilayer stiffness. Comparisons between experiments are complicated by the fact that a new cantilever is needed for each run to prevent contamination. This results in slightly different values of maximum force in each experiment (as can be seen by comparing the scales for FIGS. 13c and 14c). Despite this complication, comparisons of the relative shift of maximum tapping force associated with the bilayer can be made. In this regard, it appears that apoE3 softens the bilayer to a greater extent than apoE4 as the relative shift in maximum tapping force is much greater.

EXAMPLE 4

Simulation Demonstrates the Applicability of SPAM Analysis in Air Using Wavelets The major difference between tapping mode in air and in fluids is manifested in the quality factor (Q) of the cantilever. In air, Q is normally on the order of 200-400, whereas in fluids it is of the order of ~1-5. Due to this increased Q, the anharmonic nature of the deflection trajectory when tapping the sample is less pronounced, which can seriously limit the use of the Fourier comb filter described hereinabove. To overcome this problem, single level and multiple level signal decomposition may be performed. One example of signal decomposition is wavelet analysis.

Wavelets are mathematical functions used to separate data into different frequency components that can be studied with an appropriate resolution matched to its scale. In comparison with traditional Fourier methods, wavelets are particularly suited to study signals that contain discontinuities and sharp spikes. There are numerous different families of wavelets, and these different families can be optimized (both individually or in combination) to analyze cantilever trajectories in AFM experiments. For the application of wavelets to the present invention, the signal is analyzed by locally decomposing it with wavelets in a similar fashion to the aforementioned sliding windowed Fourier transform. The wavelet window is moved along the signal and for each position cross-correlation coefficients are computed. This operation is then repeated but with a stretched (longer) wavelet. This procedure does an appreciably better job in preserving local features of the cantilever trajectories obtained from high Q signals in comparison to Fourier analysis.

Figure 15:
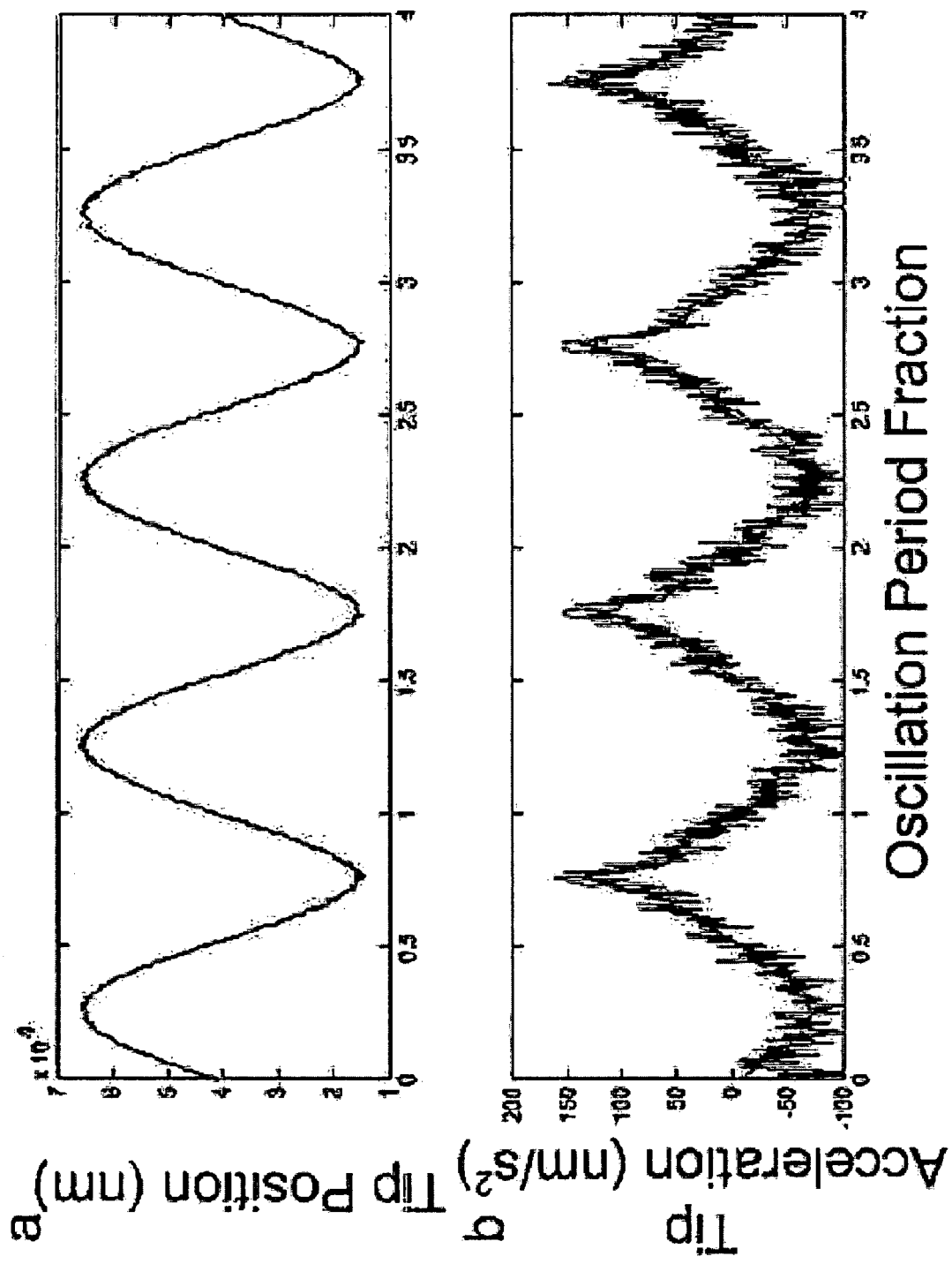
FIG. 15a illustrates a simulated cantilever trajectory for conditions corresponding to operating tapping mode AFM in air with 5% noise.
FIG. 15b illustrates reconstructed tip acceleration trajectory from a fourth level psi wavelet analysis.

As with Fourier analysis, this can be used for filtering by decomposition of a signal into different scale (frequency) components followed by reconstruction, from a limited set of components, with undesired features discarded. The filtering cutoff moves to lower and lower frequencies when reconstruction is performed from increasingly deeper levels of decomposition. This works very well in filtering the trajectories to allow for analysis based on equation 4. FIG. 15a illustrates a simulated cantilever trajectory for conditions corresponding to operating tapping mode AFM in air with 5% noise. FIG. 15b illustrates reconstructed tip acceleration trajectory from a fourth level psi wavelet analysis. By use of wavelet filtering, the time-resolved acceleration of the cantilever was recovered from the deflection signal.

Signal decomposition (e.g., wavelets) may be performed by itself or in combination with the Fourier transform and comb filter embodiments of the present invention, and can be used to filter the deflection trajectories in air and recover the time-resolved tip/sample force interaction.

EXAMPLE 5

Application of SPAM in Air Using Wavelet Analysis on Actual Force Curves

Figure 16:
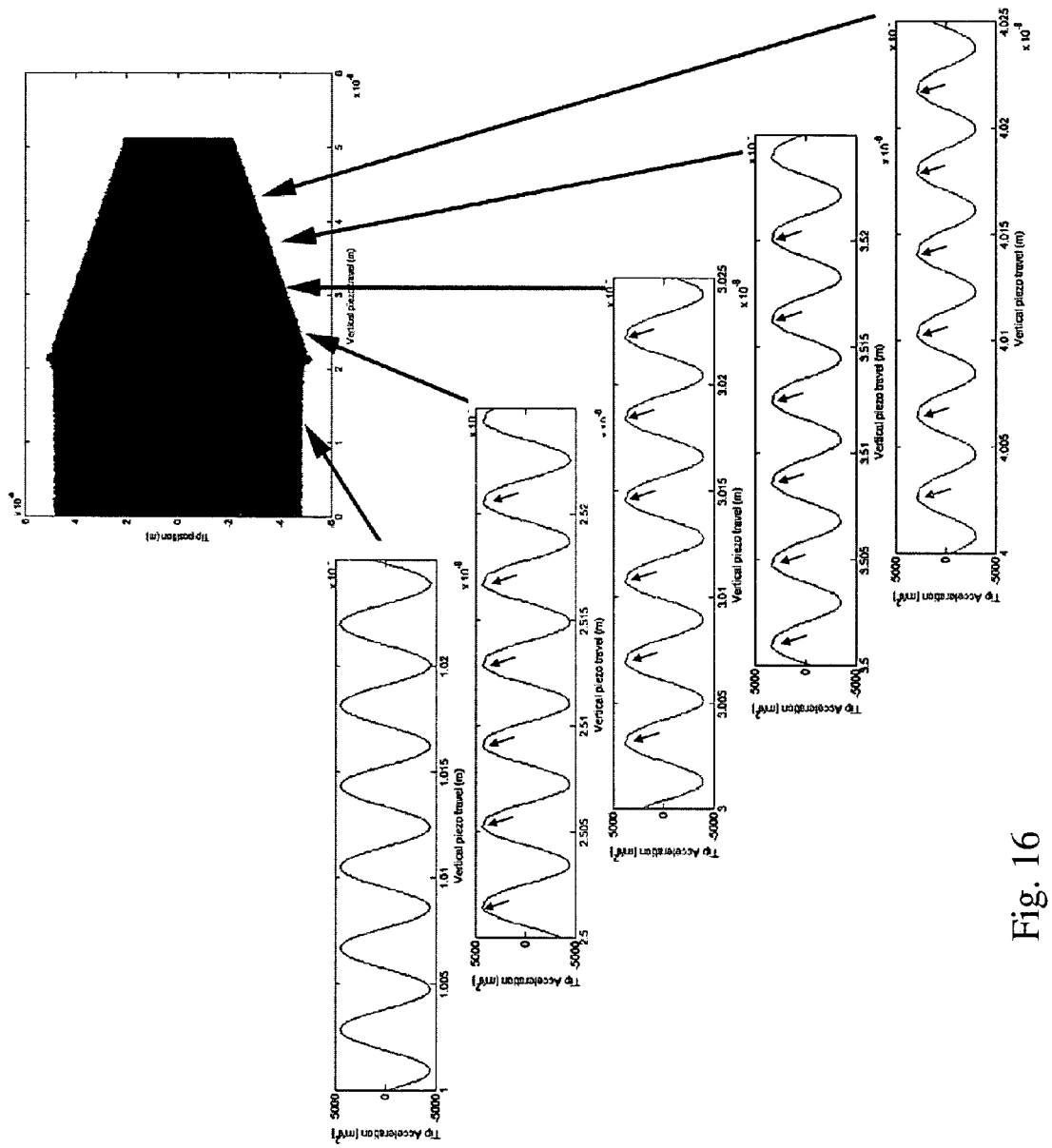
FIG. 16 illustrates TMAFM curve acquired in air with a silicon cantilever, $k=0.65$ N/m, on highly oriented pyrolytic graphite.

FIG. 16 illustrates the use of wavelets according to the present invention. The top portion of FIG. 16 illustrates the TMAFM cantilever deflection trajectory acquired in a so-called "force curve" experiment in air with a silicon cantilever, k=0.65 N/m, on highly oriented pyrolytic graphite. The deflection trajectories reflect changes associated with moving the cantilever closer to the surface. The large arrows point to parts of the cantilever deflection trajectory that were used in the calculations. The small arrows point to acceleration components (tapping force spikes) originated during tip/sample contact in each tapping event. As the cantilever was oscillated at a distance closer to the graphite surface, the amplitude of the cantilever oscillation decreased. The decrease of tapping amplitude is caused by the restriction on cantilever oscillation by the sample surface. Thus, lower cantilever oscillation amplitude corresponds to more severe restriction and higher tip-sample forces. After filtering the cantilever trajectory using wavelet analysis, the tip acceleration indeed displayed changes indicating this kind of behavior. In FIG. 16, the cantilever trajectory is shown, and the amplitude decreases as the cantilever is moved closer to the surface. A series of reconstructed acceleration trajectories are also shown for several different portions of the cantilever trajectory (indicated by the arrows). These acceleration trajectories display the appropriate changes at the top of each cycle corresponding to the distance from the surface.

The present invention is applicable to many methods, apparatuses, and technologies. The descriptions of the present invention has, in some cases, been simplified to illustrate only those elements that are relevant to a clear understanding of the present invention, while eliminating, for purpose of clarity, other elements. Those of ordinary skill in the art, upon considering the present description of the invention, will recognize that other elements may be desirable in certain applications of the present invention. For example, such a technique, as described herein, could be used to detect specific binding of functionalized tips on surfaces, i.e. tips functionalized with a specific antibody binding its corresponding antigen on a surface. Furthermore, the composition and components of the present invention may be generally described and embodied in forms and applied to end uses that are not specifically and expressly described herein. For example, one skilled in the art will appreciate that the present invention may be used to study surface and sample properties other than those specifically identified herein. In addition, the examples provided herein are illustrative and not limiting, and other variations and modifications of the present invention are contemplated. Those and other variations and modifications of the present invention are possible and contemplated, and it is intended that the foregoing specification and the following claims cover such modifications and variations.

The invention claimed is:

1. A method for proximal probing with an oscillating probe, comprising:
measuring motion of the oscillating probe;
producing a signal indicative of motion of the oscillating probe;
filtering the signal indicative of motion of the oscillating probe, wherein filtering includes performing signal decomposition to produce a filtered signal;
calculating a second derivative of the filtered signal.

2. The method of claim 1, wherein measuring the motion of the oscillating probe includes measuring an oscillating probe as in tapping mode atomic force microscopy.

3. The method of claim 1, wherein measuring the motion of the oscillating probe includes measuring an oscillating probe in non-contact proximal probing.

4. The method of claim 1, wherein measuring motion of the oscillating probe includes measuring deflection of the oscillating probe.

5. The method of claim 1, wherein performing signal decomposition includes performing multi-level signal decomposition.

6. The method of claim 1, wherein performing signal decomposition includes performing wavelet analysis.

7. The method of claim 6, wherein performing wavelet analysis includes performing multi-level wavelet analysis.

8. The method of claim 1, further comprising calculating tip/sample force using based on the second derivative of the filtered signal.

9. The method of claim 1, further comprising calculating local sample modulus using the filtered signal.

10. The method of claim 1, further comprising calculating local sample adhesion using the filtered signal.

11. The method of claim 1, further comprising calculating viscoelastic properties using the filtered signal.

12. The method of claim 1, further comprising oscillating the probe in a liquid.

13. The method of claim 1, further comprising oscillating the probe in a gas.

14. The method of claim 1, further comprising oscillating the probe in a vacuum.

15. The method of claim 1, wherein the probe includes a functionalized attachment and further comprising calculating interactions between the functionalized attachment and a surface.

16. The method of claim 15, wherein calculating interactions includes calculating attractive interactions.

17. The method of claim 15, wherein calculating interactions includes calculating repulsive interactions.

18. An apparatus, comprising:
a proximal probe including an oscillating probe and including an output port for carrying a probe motion signal;
a signal filter having an input connected to the output of the proximal probe and including a signal decomposer;
a signal processor connected to the signal filter, receiving a filtered signal from the signal filter, and including computer readable instructions which, when executed by the signal processor, cause the signal processor to calculate a second derivative of the filtered signal.

19. The apparatus of claim 18, wherein the proximal probe is an atomic force microscope.

20. The apparatus of claim 18, wherein the signal decomposer includes a signal processor including computer readable instructions which, when executed, causes a signal at the input to be decomposed and produces a filtered signal.

21. The apparatus of claim 18, wherein the signal decomposer is a multiple level signal decomposer.

22. The apparatus of claim 20, wherein the signal processor performs wavelet analysis.

23. The method of claim 1, wherein filtering the signal includes comb-filtering the signal to retain harmonic frequencies of the probe and exclude non-harmonic frequencies of the probe.

24. The method of claim 1, wherein filtering includes:
   decomposing the signal into different frequency components;

discarding undesired frequency components to create a limited set of frequency components;

reconstructing the signal from the limited set of frequency components.

* * * * *

UNITED STATES PATENT AND TRADEMARK OFFICE
CERTIFICATE OF CORRECTION

PATENT NO. : 7,464,583 B1
APPLICATION NO. : 11/450074
DATED : December 16, 2008
INVENTOR(S) : Tomasz P. Kowalewski et al.

It is certified that error appears in the above-identified patent and that said Letters Patent is hereby corrected as shown below:

Column 1, ln. 34, delete "piezoelectric" and insert -- piezolectric --.

Column 7, ln. 66, delete "includes" and insert -- included --.

Column 10, ln. 32, at end of paragraph after "elsewhere.", insert -- Steps formed by bilayer patches on mica were simulated with a surface modulus of 1 GPa. --

Column 10, ln. 33, delete "Steps formed by bilayer patches on mica were simulated with a surface modulus of 1 GPa".

Column 11, ln. 30, delete "fob" and insert -- for --.

Signed and Sealed this

Sixteenth Day of February, 2010

David J. Kappos
*Director of the United States Patent and Trademark Office*